United States Patent
Von Horsten et al.

(10) Patent No.: US 9,765,158 B2
(45) Date of Patent: Sep. 19, 2017

(54) METHODS FOR PREPARATION OF FUCOSE-LINKED SITE SPECIFIC CONJUGATES OF PROTEINS WITH TOXINS, ADJUVANTS, DETECTION LABELS AND PHARMACOKINETIC HALF LIFE EXTENDERS

(75) Inventors: Hans Henning Von Horsten, Berlin (DE); Volker Sandig, Berlin (DE); Ingo Jordan, Berlin (DE); Karsten Winkler, Berlin (DE)

(73) Assignee: Probiogen AG, Berlin (DE)

( * ) Notice: Subject to any disclaimer, the term of this patent is extended or adjusted under 35 U.S.C. 154(b) by 727 days.

(21) Appl. No.: 14/123,079

(22) PCT Filed: May 31, 2012

(86) PCT No.: PCT/EP2012/060286
§ 371 (c)(1),
(2), (4) Date: Apr. 2, 2014

(87) PCT Pub. No.: WO2012/164034
PCT Pub. Date: Dec. 6, 2012

(65) Prior Publication Data
US 2014/0221627 A1 Aug. 7, 2014

Related U.S. Application Data

(60) Provisional application No. 61/491,456, filed on May 31, 2011.

(51) Int. Cl.
| | | |
|---|---|---|
| *C12P 21/06* | (2006.01) | |
| *C12N 15/00* | (2006.01) | |
| *C07K 17/10* | (2006.01) | |
| *A61K 47/48* | (2006.01) | |
| *C07K 16/00* | (2006.01) | |
| *B82Y 5/00* | (2011.01) | |

(52) U.S. Cl.
CPC ........ *C07K 17/10* (2013.01); *A61K 47/48376* (2013.01); *A61K 47/48753* (2013.01); *B82Y 5/00* (2013.01); *C07K 16/00* (2013.01); *C07K 2317/14* (2013.01); *C07K 2317/41* (2013.01)

(58) Field of Classification Search
None
See application file for complete search history.

(56) References Cited

U.S. PATENT DOCUMENTS

| | | | |
|---|---|---|---|
| 8,642,292 B2 * | 2/2014 | Sandig | C07K 16/00 435/252.3 |
| 2008/0241856 A1 | 10/2008 | Wong et al. | |
| 2014/0221627 A1 * | 8/2014 | Von Horsten | A61K 47/48376 530/391.9 |

FOREIGN PATENT DOCUMENTS

| | | |
|---|---|---|
| WO | 99/24472 A2 | 5/1999 |
| WO | 2007/095506 A1 | 8/2007 |
| WO | 2011/035884 A1 | 3/2011 |

OTHER PUBLICATIONS

Sawa, et al., "Glycoproteomic probes for fluorescent imaging of fucosylated glycans in vivo," *Proceedings of the National Academy of Sciences*, vol. 103(33), pp. 12371-12376 (2006).
International Search Report for PCT/EP2012/060286, mailed Aug. 31, 2012, 5 pages.

* cited by examiner

*Primary Examiner* — Michael Burkhart
(74) *Attorney, Agent, or Firm* — Kilpatrick Townsend & Stockton LLP

(57) ABSTRACT

The present invention relates to eukaryotic cells for producing molecules having an atypical fucose analog on their glycomoieties and/or amino acids. It also relates to methods for producing molecules having an atypical fucose analog on their glycomoieties and/or amino acids and to molecules obtainable by said methods. It further relates to methods for producing conjugates comprising molecules having an atypical fucose analog on their glycomoieties and/or amino acids and pharmaceutical active compounds and to conjugates obtainable by said methods. In addition, the present invention relates to specific conjugates.

18 Claims, 3 Drawing Sheets

SEQUENCE LISTING

```
<160> NUMBER OF SEQ ID NOS: 10

<210> SEQ ID NO 1
<211> LENGTH: 304
<212> TYPE: PRT
<213> ORGANISM: Pseudomonas aeruginosa
<220> FEATURE:
<223> OTHER INFORMATION: Pseudomonas aeruginosa strain PAO1
      oxidoreductase Rmd, GDP-6-deoxy-D-lyxo-4-hexulose reductase (RMD),
      locus PA5454

<400> SEQUENCE: 1

Met Thr Gln Arg Leu Phe Val Thr Gly Leu Ser Gly Phe Val Gly Lys
1               5                   10                  15

His Leu Gln Ala Tyr Leu Ala Ala Ala His Thr Pro Trp Ala Leu Leu
            20                  25                  30

Pro Val Pro His Arg Tyr Asp Leu Leu Glu Pro Asp Ser Leu Gly Asp
        35                  40                  45

Leu Trp Pro Glu Leu Pro Asp Ala Val Ile His Leu Ala Gly Gln Thr
    50                  55                  60

Tyr Val Pro Glu Ala Phe Arg Asp Pro Ala Arg Thr Leu Gln Ile Asn
65                  70                  75                  80

Leu Leu Gly Thr Leu Asn Leu Leu Gln Ala Leu Lys Ala Arg Gly Phe
                85                  90                  95
```

-continued

```
Ser Gly Thr Phe Leu Tyr Ile Ser Ser Gly Asp Val Tyr Gly Gln Val
            100                 105                 110

Ala Glu Ala Ala Leu Pro Ile His Glu Glu Leu Ile Pro His Pro Arg
        115                 120                 125

Asn Pro Tyr Ala Val Ser Lys Leu Ala Ala Glu Ser Leu Cys Leu Gln
    130                 135                 140

Trp Gly Ile Thr Glu Gly Trp Arg Val Leu Val Ala Arg Pro Phe Asn
145                 150                 155                 160

His Ile Gly Pro Gly Gln Lys Asp Ser Phe Val Ile Ala Ser Ala Ala
                165                 170                 175

Arg Gln Ile Ala Arg Met Lys Gln Gly Leu Gln Ala Asn Arg Leu Glu
            180                 185                 190

Val Gly Asp Ile Asp Val Ser Arg Asp Phe Leu Asp Val Gln Asp Val
        195                 200                 205

Leu Ser Ala Tyr Leu Arg Leu Leu Ser His Gly Glu Ala Gly Ala Val
    210                 215                 220

Tyr Asn Val Cys Ser Gly Gln Glu Gln Lys Ile Arg Glu Leu Ile Glu
225                 230                 235                 240

Leu Leu Ala Asp Ile Ala Gln Val Glu Leu Glu Ile Val Gln Asp Pro
                245                 250                 255

Ala Arg Met Arg Arg Ala Glu Gln Arg Arg Val Arg Gly Ser His Ala
            260                 265                 270

Arg Leu His Asp Thr Thr Gly Trp Lys Pro Glu Ile Thr Ile Lys Gln
        275                 280                 285

Ser Leu Arg Ala Ile Leu Ser Asp Trp Glu Ser Arg Val Arg Glu Glu
    290                 295                 300
```

<210> SEQ ID NO 2
<211> LENGTH: 294
<212> TYPE: PRT
<213> ORGANISM: Actinobacillus actinomycetemcomitans
<220> FEATURE:
<223> OTHER INFORMATION: GDP-6-deoxy-D-talose synthetase (GTS)

<400> SEQUENCE: 2

```
Met Lys Ile Leu Val Thr Gly Gly Ser Gly Phe Ile Gly Lys Asn Leu
1               5                   10                  15

Ile Tyr Leu Leu Arg Glu Lys Arg Glu Phe Glu Val Phe Gly Ala Thr
            20                  25                  30

Val Glu Glu Thr Met Asp Leu Thr Asn Pro Cys Ser Val Gln Ser Val
        35                  40                  45

Leu Glu Lys Thr Lys Pro Asp Phe Ile Val His Leu Ala Ala Leu Thr
    50                  55                  60

Phe Val Pro Asn Asn Asn Pro Ile Thr Phe Tyr Leu Val Asn Thr Ile
65                  70                  75                  80

Gly Thr Glu Asn Leu Leu Arg Ser Ile Val Asp Leu Asn Val Ala Lys
                85                  90                  95

Leu Gly Val Leu Cys Phe Ser Thr Ala Gly Ile Tyr Gly Ile Gln Glu
            100                 105                 110

Thr Lys Leu Leu Ser Glu Ser Leu Thr Pro Lys Pro Val Asn His Tyr
        115                 120                 125

Ser Met Ser Lys His Cys Met Glu His Ile Val Asn Lys Tyr Arg Cys
    130                 135                 140

Phe Arg Gly Ile Thr Val Val Arg Pro Phe Asn Val Leu Gly Leu Gly
145                 150                 155                 160
```

```
Gln Asn Ile Asn Phe Leu Val Pro Lys Met Val Ser Ala Phe Val Lys
                165                 170                 175

Lys Asp Lys Thr Ile Glu Leu Gly Asn Leu Asp Ser Val Arg Asp Phe
            180                 185                 190

Ile Ser Val Asn Asp Cys Cys Asp Ile Ile Tyr Arg Leu Ile Ser Lys
        195                 200                 205

Leu Ile Glu Asn Glu Thr Ile Asn Ile Cys Thr Gly Ile Gly Tyr Ser
    210                 215                 220

Val Tyr Gln Ile Phe Gln Leu Leu Cys Glu Ile Ser Met His Gln Met
225                 230                 235                 240

Glu Ile Lys Gln Asn Glu Leu Phe Val Arg His Asp Asp Ile Pro Gln
                245                 250                 255

Met Ile Gly Asp Pro Ser Lys Leu Leu Asn Val Leu Gly Asn Asp Tyr
            260                 265                 270

Arg Phe Thr Ser Val Arg Ala Ile Leu Glu Glu Met Tyr Lys Asn Arg
        275                 280                 285

Leu Leu Glu Leu Ser Ile
    290

<210> SEQ ID NO 3
<211> LENGTH: 367
<212> TYPE: PRT
<213> ORGANISM: Vibrio cholerae
<220> FEATURE:
<223> OTHER INFORMATION: GDP-perosamine synthetase (Per)

<400> SEQUENCE: 3

Met Ile Pro Val Tyr Glu Pro Ser Leu Asp Gly Asn Glu Arg Lys Tyr
1               5                   10                  15

Leu Asn Asp Cys Ile Asp Ser Gly Trp Val Ser Arg Gly Lys Tyr
            20                  25                  30

Ile Asp Arg Phe Glu Thr Glu Phe Ala Glu Phe Leu Lys Val Lys His
        35                  40                  45

Ala Thr Thr Val Ser Asn Gly Thr Val Ala Leu His Leu Ala Met Ser
    50                  55                  60

Ala Leu Gly Ile Thr Gln Gly Asp Glu Val Ile Val Pro Thr Phe Thr
65                  70                  75                  80

Tyr Val Ala Ser Val Asn Thr Ile Val Gln Cys Gly Ala Leu Pro Val
                85                  90                  95

Phe Ala Glu Ile Glu Gly Glu Ser Leu Gln Val Ser Val Glu Asp Val
            100                 105                 110

Lys Arg Lys Ile Asn Lys Lys Thr Lys Ala Val Met Ala Val His Ile
        115                 120                 125

Tyr Gly Gln Ala Cys Asp Ile Gln Ser Leu Arg Asp Leu Cys Asp Glu
    130                 135                 140

His Gly Leu Tyr Leu Ile Glu Asp Cys Ala Glu Ala Ile Gly Thr Ala
145                 150                 155                 160

Val Asn Gly Lys Lys Val Gly Thr Phe Gly Asp Val Ser Thr Phe Ser
                165                 170                 175

Phe Phe Gly Asn Lys Thr Ile Thr Ser Gly Glu Gly Gly Met Val Val
            180                 185                 190

Ser Asn Ser Asp Ile Ile Ile Asp Lys Cys Leu Arg Leu Lys Asn Gln
        195                 200                 205

Gly Val Val Ala Gly Lys Arg Tyr Trp His Asp Leu Val Ala Tyr Asn
    210                 215                 220
```

-continued

```
Tyr Arg Met Thr Asn Leu Cys Ala Ala Ile Gly Val Ala Gln Leu Glu
225                 230                 235                 240

Arg Val Asp Lys Ile Ile Lys Arg Lys Arg Asp Ile Ala Glu Ile Tyr
            245                 250                 255

Arg Ser Glu Leu Ala Gly Leu Pro Met Gln Val His Lys Glu Ser Asn
            260                 265                 270

Gly Thr Phe His Ser Tyr Trp Leu Thr Ser Ile Ile Leu Asp Gln Glu
            275                 280                 285

Phe Glu Val His Arg Asp Gly Leu Met Thr Phe Leu Glu Asn Asn Asp
290                 295                 300

Ile Glu Ser Arg Pro Phe Phe Tyr Pro Ala His Thr Leu Pro Met Tyr
305                 310                 315                 320

Glu His Leu Ala Glu Lys Thr Ala Phe Pro Leu Ser Asn Ser Tyr Ser
            325                 330                 335

His Arg Gly Ile Asn Leu Pro Ser Trp Pro Gly Leu Cys Asp Asp Gln
            340                 345                 350

Val Lys Glu Ile Cys Asn Cys Ile Lys Asn Tyr Phe Asn Cys Ile
            355                 360                 365
```

<210> SEQ ID NO 4
<211> LENGTH: 388
<212> TYPE: PRT
<213> ORGANISM: Escherichia coli
<220> FEATURE:
<223> OTHER INFORMATION: GDP-4-keto-6-deoxymannose-3-dehydratase (ColD)

<400> SEQUENCE: 4

```
Met Ile Asn Tyr Pro Leu Ala Ser Ser Thr Trp Asp Asp Leu Glu Tyr
1               5                   10                  15

Lys Ala Ile Gln Ser Val Leu Asp Ser Lys Met Phe Thr Met Gly Glu
            20                  25                  30

Tyr Val Lys Gln Tyr Glu Thr Gln Phe Ala Lys Thr Phe Gly Ser Lys
        35                  40                  45

Tyr Ala Val Met Val Ser Ser Gly Ser Thr Ala Asn Leu Leu Met Ile
    50                  55                  60

Ala Ala Leu Phe Phe Thr Lys Lys Pro Arg Leu Lys Lys Gly Asp Glu
65                  70                  75                  80

Ile Ile Val Pro Ala Val Ser Trp Ser Thr Thr Tyr Tyr Pro Leu Gln
                85                  90                  95

Gln Tyr Gly Leu Arg Val Lys Phe Val Asp Ile Asp Ile Asn Thr Leu
            100                 105                 110

Asn Ile Asp Ile Glu Ser Leu Lys Glu Ala Val Thr Asp Ser Thr Lys
        115                 120                 125

Ala Ile Leu Thr Val Asn Leu Leu Gly Asn Pro Asn Phe Asp Glu
    130                 135                 140

Ile Asn Lys Ile Ile Gly Gly Arg Asp Ile Ile Leu Leu Glu Asp Asn
145                 150                 155                 160

Cys Glu Ser Met Gly Ala Thr Phe Asn Asn Lys Cys Ala Gly Thr Phe
                165                 170                 175

Gly Leu Met Gly Thr Phe Ser Ser Phe Tyr Ser His His Ile Ala Thr
            180                 185                 190

Met Glu Gly Gly Cys Ile Val Thr Asp Asp Glu Glu Ile Tyr His Ile
        195                 200                 205

Leu Leu Cys Ile Arg Ala His Gly Trp Thr Arg Asn Leu Pro Lys Lys
    210                 215                 220
```

```
Asn Lys Val Thr Gly Val Lys Ser Asp Asp Gln Phe Glu Glu Ser Phe
225                 230                 235                 240

Lys Phe Val Leu Pro Gly Tyr Asn Val Arg Pro Leu Glu Met Ser Gly
                245                 250                 255

Ala Ile Gly Ile Glu Gln Leu Lys Lys Leu Pro Arg Phe Ile Ser Val
            260                 265                 270

Arg Arg Lys Asn Ala Glu Tyr Phe Leu Asp Lys Phe Lys Asp His Pro
        275                 280                 285

Tyr Leu Asp Val Gln Gln Glu Thr Gly Glu Ser Ser Trp Phe Gly Phe
    290                 295                 300

Ser Phe Ile Ile Lys Lys Asp Ser Gly Val Ile Arg Lys Gln Leu Val
305                 310                 315                 320

Glu Asn Leu Asn Ser Ala Gly Ile Glu Cys Arg Pro Ile Val Thr Gly
                325                 330                 335

Asn Phe Leu Lys Asn Thr Asp Val Leu Lys Tyr Phe Asp Tyr Thr Val
                340                 345                 350

His Asn Asn Val Asp Asn Ala Glu Tyr Leu Asp Lys Asn Gly Leu Phe
            355                 360                 365

Val Gly Asn His Gln Ile Glu Leu Phe Asp Gly Ile Asp Tyr Leu Arg
    370                 375                 380

Glu Val Leu Lys
385

<210> SEQ ID NO 5
<211> LENGTH: 321
<212> TYPE: PRT
<213> ORGANISM: Cricetulus griseus
<220> FEATURE:
<223> OTHER INFORMATION: Chinese hamster wild-type GDP-fucose synthetase
      (GFS)

<400> SEQUENCE: 5

Met Gly Glu Pro Gln Gly Ser Arg Arg Ile Leu Val Thr Gly Gly Ser
1               5                   10                  15

Gly Leu Val Gly Arg Ala Ile Gln Lys Val Val Ala Asp Gly Ala Gly
            20                  25                  30

Leu Pro Gly Glu Glu Trp Val Phe Val Ser Ser Lys Asp Ala Asp Leu
        35                  40                  45

Thr Asp Ala Ala Gln Thr Gln Ala Leu Phe Gln Lys Val Gln Pro Thr
    50                  55                  60

His Val Ile His Leu Ala Ala Met Val Gly Gly Leu Phe Arg Asn Ile
65                  70                  75                  80

Lys Tyr Asn Leu Asp Phe Trp Arg Lys Asn Val His Ile Asn Asp Asn
                85                  90                  95

Val Leu His Ser Ala Phe Glu Val Gly Thr Arg Lys Val Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
```

```
              180                 185                 190
His Lys Val His Leu Ala Lys Ser Asn Gly Ser Ala Leu Thr Val Trp
            195                 200                 205
Gly Thr Gly Lys Pro Arg Arg Gln Phe Ile Tyr Ser Leu Asp Leu Ala
            210                 215                 220
Arg Leu Phe Ile Trp Val Leu Arg Glu Tyr Asn Glu Val Glu Pro Ile
225                 230                 235                 240
Ile Leu Ser Val Gly Glu Glu Asp Glu Val Ser Ile Lys Glu Ala Ala
                245                 250                 255
Glu Ala Val Val Glu Ala Met Asp Phe Cys Gly Glu Val Thr Phe Asp
                260                 265                 270
Ser Thr Lys Ser Asp Gly Gln Tyr Lys Lys Thr Ala Ser Asn Gly Lys
            275                 280                 285
Leu Arg Ala Tyr Leu Pro Asp Phe Arg Phe Thr Pro Phe Lys Gln Ala
            290                 295                 300
Val Lys Glu Thr Cys Ala Trp Phe Thr Asp Asn Tyr Glu Gln Ala Arg
305                 310                 315                 320
Lys

<210> SEQ ID NO 6
<211> LENGTH: 314
<212> TYPE: PRT
<213> ORGANISM: Artificial Sequence
<220> FEATURE:
<223> OTHER INFORMATION: Cricetulus griseus (Chinese hamster) GDP-fucose
      synthetase Cys109Ser- (GFS-Cys109Ser) mutant

<400> SEQUENCE: 6

Met Arg Ile Leu Val Thr Gly Gly Ser Gly Leu Val Gly Arg Ala Ile
1               5                   10                  15
Gln Lys Val Val Ala Asp Gly Ala Gly Leu Pro Gly Glu Glu Trp Val
                20                  25                  30
Phe Val Ser Ser Lys Asp Ala Asp Leu Thr Asp Ala Ala Gln Thr Gln
            35                  40                  45
Ala Leu Phe Gln Lys Val Gln Pro Thr His Val Ile His Leu Ala Ala
        50                  55                  60
Met Val Gly Gly Leu Phe Arg Asn Ile Lys Tyr Asn Leu Asp Phe Trp
65                  70                  75                  80
Arg Lys Asn Val His Ile Asn Asp Asn Val Leu His Ser Ala Phe Glu
                85                  90                  95
Val Gly Thr Arg Lys Val Val Ser Cys Leu Ser Thr Ser Ile Phe Pro
                100                 105                 110
Asp Lys Thr Thr Tyr Pro Ile Asp Glu Thr Met Ile His Asn Gly Pro
            115                 120                 125
Pro His Ser Ser Asn Phe Gly Tyr Ser Tyr Ala Lys Arg Met Ile Asp
        130                 135                 140
Val Gln Asn Arg Ala Tyr Phe Gln Gln His Gly Cys Thr Phe Thr Ala
145                 150                 155                 160
Val Ile Pro Thr Asn Val Phe Gly Pro His Asp Asn Phe Asn Ile Glu
                165                 170                 175
Asp Gly His Val Leu Pro Gly Leu Ile His Lys Val His Leu Ala Lys
                180                 185                 190
Ser Asn Gly Ser Ala Leu Thr Val Trp Gly Thr Gly Lys Pro Arg Arg
            195                 200                 205
Gln Phe Ile Tyr Ser Leu Asp Leu Ala Arg Leu Phe Ile Trp Val Leu
```

```
            210                 215                 220
Arg Glu Tyr Asn Glu Val Glu Pro Ile Ile Leu Ser Val Gly Glu Glu
225                 230                 235                 240

Asp Glu Val Ser Ile Lys Glu Ala Ala Glu Ala Val Val Glu Ala Met
                245                 250                 255

Asp Phe Cys Gly Glu Val Thr Phe Asp Ser Thr Lys Ser Asp Gly Gln
                260                 265                 270

Tyr Lys Lys Thr Ala Ser Asn Gly Lys Leu Arg Ala Tyr Leu Pro Asp
            275                 280                 285

Phe Arg Phe Thr Pro Phe Lys Gln Ala Val Lys Glu Thr Cys Ala Trp
290                 295                 300

Phe Thr Asp Asn Tyr Glu Gln Ala Arg Lys
305                 310

<210> SEQ ID NO 7
<211> LENGTH: 307
<212> TYPE: PRT
<213> ORGANISM: Escherichia coli
<220> FEATURE:
<223> OTHER INFORMATION: GDP-L-colitose synthase (ColC)

<400> SEQUENCE: 7

Met Lys Ile Leu Leu Thr Gly Ser Thr Gly Met Val Gly Arg Asn Ile
1               5                   10                  15

Val Asp Asn Asn Ser Asn Lys Tyr Glu Leu Leu Cys Pro Thr Ser
            20                  25                  30

Ser Glu Leu Asn Leu Leu Asp Asn Lys Ala Val His Asp Tyr Ile Thr
            35                  40                  45

Cys His Ser Pro Asp Leu Ile Ile His Ala Ala Gly Leu Val Gly Gly
        50                  55                  60

Ile Gln Ala Asn Ile Lys Arg Pro Val Asp Phe Leu Val Ser Asn Leu
65                  70                  75                  80

Lys Met Gly Val Asn Ile Val Asn Glu Ala Lys Asn Cys Gly Val Lys
                85                  90                  95

Asn Phe Ile Asn Leu Gly Ser Ser Cys Met Tyr Pro Lys Gly Ile Asp
            100                 105                 110

Thr Ala Ile Ser Glu Asp Ala Leu Leu Thr Gly Lys Leu Glu His Thr
        115                 120                 125

Asn Glu Gly Tyr Ala Leu Ala Lys Ile Thr Val Ala Lys Leu Cys Glu
    130                 135                 140

Tyr Ile Thr Lys Glu Ser Glu Gly Tyr His Tyr Lys Thr Ile Ile Pro
145                 150                 155                 160

Cys Asn Leu Tyr Gly Lys Tyr Asp Lys Phe Asp Glu His Ser Ser His
                165                 170                 175

Met Ile Pro Ala Val Ile Asn Arg Ile His Asn Ala Lys Val Asn Asn
            180                 185                 190

Ile Lys Leu Ile Glu Ile Trp Gly Asp Gly Glu Ser Arg Arg Glu Phe
        195                 200                 205

Met Tyr Ala Glu Asp Phe Ala Asn Phe Ile Tyr Gln Ala Ile Pro Asn
    210                 215                 220

Ile Gln Arg Leu Pro Cys Met Leu Asn Val Gly Leu Gly His Asp Phe
225                 230                 235                 240

Ser Ile Asn Asp Tyr Tyr Lys Val Ile Ala Glu Glu Ile Gly Tyr Lys
                245                 250                 255

Gly Ser Phe Thr His Asp Leu Thr Lys Pro Val Gly Met Arg Arg Lys
```

```
                   260                 265                 270
Leu Val Asp Ile Thr Leu Leu Ser Glu Phe Gly Trp Lys Tyr Gln Phe
            275                 280                 285

Glu Leu Arg Asp Gly Ile Lys Glu Thr Tyr Lys Tyr Tyr Leu Glu Asn
            290                 295                 300

Val Tyr Lys
305

<210> SEQ ID NO 8
<211> LENGTH: 330
<212> TYPE: PRT
<213> ORGANISM: Homo sapiens
<220> FEATURE:
<223> OTHER INFORMATION: IgG1 antibody heavy chain constant domain (CH
      domain) with G161 and Y278 substituted with Ser (IgG1 CH Allele
      01, human)

<400> SEQUENCE: 8

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 330
<212> TYPE: PRT
<213> ORGANISM: Homo sapiens
<220> FEATURE:
<223> OTHER INFORMATION: IgG1 antibody heavy chain constant domain (CH
      domain) with G161 and Y278 substituted with Ser (IgG1 CH Allele
      02, human)

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

```
Gln Lys Ser Leu Ser Leu Ser Pro Gly Lys
            325                 330

<210> SEQ ID NO 10
<211> LENGTH: 25
<212> TYPE: PRT
<213> ORGANISM: Artificial Sequence
<220> FEATURE:
<223> OTHER INFORMATION: EGF-like repeat

<400> SEQUENCE: 10

Asp Gly Asp Gly Cys Ala Ser Ser Pro Cys Gln Asn Gly Gly Ser Cys
1               5                   10                  15

Lys Asp Gln Leu Gln Ser Tyr Ile Cys
            20                  25
```

METHODS FOR PREPARATION OF FUCOSE-LINKED SITE SPECIFIC CONJUGATES OF PROTEINS WITH TOXINS, ADJUVANTS, DETECTION LABELS AND PHARMACOKINETIC HALF LIFE EXTENDERS

CROSS-REFERENCE TO RELATED APPLICATIONS

This application is the U.S. National Stage entry of PCT/EP2012/060286, filed May 31, 2012, which claims priority to U.S. Provisional Application No. 61/491,456, filed May 31, 2011.

REFERENCE TO A SEQUENCE LISTING

This application includes a Sequence Listing named "95697-894485.txt" created on Jan. 29, 2014 and containing 27,000 bytes. The material contained in this text file is incorporated by reference in its entirety for all purposes.

The present invention relates to eukaryotic cells for producing molecules having an atypical fucose analogue on their glycomoieties and/or amino acids. It also relates to methods for producing molecules having an atypical fucose analogue on their glycomoieties and/or amino acids and to molecules obtainable by said methods. It further relates to methods for producing conjugates comprising molecules having an atypical fucose analogue on their glycomoieties and/or amino acids and pharmaceutical active compounds and to conjugates obtainable by said methods. In addition, the present invention relates to specific conjugates.

BACKGROUND OF THE INVENTION

Today, insertion of predetermined points of attachment for an active moiety plays a key role for efficient binding of biological products. Conjugation of proteins and functional compounds is typically accomplished through covalent attachment of the functional compound to side chains of amino acid residues. Classical bioconjugate technologies are known to work in a non-site-restricted fashion which makes it difficult to avoid undesirable couplings at critical amino acid residues and also poses a risk for lot consistency due to inherent heterogeneity of the outcome of the coupling reaction. Non-selective chemical coupling via hydroxyl-groups of protein-linked carbohydrate structures requires harsh reaction conditions and bears the risk of unwanted modification of amino acid side chains of the protein. Critical residues that may be affected by undesirable coupling or modification include amino acid side chains important for overall product thermal stability and aggregation propensity. In case of antibodies, unwanted conjugation to amino acid side chains within or in proximity to the complementarity determining regions (CDRs) may lead to reduced affinity and heterogeneous antigen-binding properties. Chemical coupling is typically accomplished via protein-linked functional groups such as primary amines, sulfhydryls, carbonyls, carbohydrates, carboxylic acids and hydroxyl groups. Reactive groups used for coupling via such functional groups include aryl azide, carbodiimide, carbonyl, diazirine, hydrazide, hydroxymethyl phosphine, imidoester, isocyanate, maleimide, N-hydroxy-succinimide ester (NHS-ester), pentafluorophenyl ester (PFP-ester), psoralen and pyridyl disulfide.

Conjugation can be easily directed at sulfhydryl groups. However, due to the reactivity of the thiol group, free thiols are rarely found in expressed proteins. Direct labeling of free thiol-groups thus relies mainly on the reduction of existing disulfide (S—S) bonds. Antibodies as one of the major groups of therapeutic proteins have been coupled to functional compounds via sulfhydryl groups in the past. Since reduction of the heavy to light chain disulfide bond occurs at approximately double the frequency of the heavy to heavy disulfide bonds, such partial reduction approaches bear the possible risk of protein fragmentation by light chain loss. (Sun, et al., Bioconjug Chem 16:1282-1290 (2005).) In particular, the thermal stability of the critical antibody CH2 domain may be negatively affected by reduction of the inter-sheet disulfide bond. Production of a homogenous product from such random-type sulfhydryl-coupling reaction is a rather complicated and inefficient process. Early preclinical versions of the cAC 10 antibody drug conjugate, a sulfhydryl-linked immunoconjugate involved linkage of eight cytotoxic drug molecules per antibody molecule (Doronina et al., Nat. Biotechnol. 21(7): 778-84 (2003)). The coupling-enabled cysteine residues were obtained by reduction of the four interchain disulfide bonds (Doronina et al., Nat. Biotechnol. 21(7): 778-84 (2003)). Incomplete reduction of disulfide bonds led to a heterogeneous mixture of incomplete conjugates with less than eight drug molecules loaded per antibody (Hamblett et. al. Effects of drug loading on the antitumor activity of a monoclonal antibody-drug conjugate. Clinical Cancer Research, 2004, 10(20):7063-70). Product homogeneity for the random sulfhydryl-coupled conjugate proofed difficult to achieve and overall yield was rather low (Hamblett et. al. 2004).

Coupling via amino-groups of lysine residues is also a common mode of producing bioconjugates of proteins and functional compounds. Most recently, a thiol-containing maytansinoid, DM1 (N-methyl-N-[3-mercapto-1-oxopropyl]-L-alanine ester of maytansinol), an analogue of the clinically-studied drug maytansine) was used to link maytansinoids to antibodies through disulfide bonds (Barginear and Budman, 2009) In the case of Trastuzumab-DM1, DM1 is linked to trastuzumab using the bifunctional reagent, SMCC(N-succinimidyl-4-maleimidomethyl-cyclohexanecarboxylate.) SMCC is first added to lysine residues on the protein to produce a linker modified antibody. Coupling of the succinimidyl-group of SMCC to lysine residues happens in a random fashion targeted at all surface exposed lysine residues of the antibody. The thiol group in DM1 is then reacted with the maleimide group of the linker to form the nonreducible thioether bond (Barginear and Budman, 2009). Maleimides react with sulfhydryls at pH 6.5-7.5 to form stable thioether bonds. At pH values>7.5, however, maleimides also react toward primary amines which can result in the production of undesired covalent protein oligomers. In addition, the random coupling of SMCC to the antibody results in a non-homogenous bioconjugate product. The C-terminal lysine of antibody heavy chains is prone to clipping during upstream cell culture production and thus further coupling heterogeneitiy may result from differentially clipped C-terminal lysine residues. Each Trastuzumab-DM1 antibody contains an average of 3.5 drug molecules (Smith S V. Technology evaluation, Hun90'-dml, immunogen. Curr Opin Mol Ther 2005; 7: 394-401.), reflecting the typical distribution from 0 to 8 drug molecules per antibody (Blattler W A, Chari R V J, Vite G D, Altmann K H, Eds. Anticancer Agents—Frontiers in Cancer Chemotherapy, American Chemical Society, Washington 2001; 317-38.). The stoichiometric molar ratio of antibody and functional compound is an important determinator of therapeutic activity and conjugate stability. Kulkarni et al. (Cancer Research 41:2700-2706 (1981)) found that the highest efficient antibody-to-toxin-ratio obtained for methotrexate was about ten methotrexate molecules per antibody, and that attempts to increase the drug-antibody molar ratio beyond this threshold decreased the yield of immunoconjugate and damaged antibody activity. Similar results have been reported by Kanellos et al. (JNC 75:319-329 (1985)).

The inherent inhomogeneity of random-coupled bioconjugate products poses a challenge for stability studies, lot consistency and in-process analytics. Production of a homogenous bioconjugate product from a random coupling reaction can only be accomplished with significant downstream effort associated with a dramatic loss of product yield. Thus, there is a need for antibodies having one or more predetermined sites for stoichiometric attachment of functional compounds.

Recently, such antibodies for predetermined, site-directed thiol-coupling were described by Seattle Genetics Inc. (United States Patent Application 2008/0305044). While this mode of coupling has all the benefits of a site-directed approach, the minor destruction of tertiary structure is likely to impact overall product thermal stability.

United States Patent Application 2010/0254943 AMINO ACID SUBSTITUTED MOLECULES and related applications belonging to the same patent family disclose a method for obtaining site specific conjugates of proteins by incorporating coupling enabled non-natural amino acids into the protein sequence and for utilizing such non-natural amino acid residues as an anchoring position for further chemical or biological modification. The amino acid position at which the non-natural amino acid is incorporated is specified by a codon that is typically used to specify a naturally occurring amino acid (such as a wobble codon, a bias codon, a sixth box codon, a 4 box codon, or any other sense codon that the host cell or in vitro translation system might be used to specify a non-natural amino acid incorporation site), or a codon which is typically a stop codon, such as amber, ochre, or opal, or a frameshift codon. In cases where in-frame stop codons are used for artificial incorporation of non-natural amino acids, the cells need to be knocked-out for the cognate release factor (or translation termination factor). Given the redundancy between the existing translation termination factors, cells will always produce both the correct full length protein containing the incorporated non-natural amino acids and also prematurely truncated versions of the target protein. This makes this type of production method for such coupling enabled proteins highly inefficient, particularly in eukaryotic expression systems where the release factor eRF1 functions as an omnipotent release factor and recognizes all three termination codons. While this method is suitable to produce proteins enabled for site directed and defined coupling, there is still a need to produce such defined coupling-enabled proteins at far higher process efficiency.

Glycan-Structures linked to naturally occupied N-glycosylation sites typically stabilize protein conformation. The size of the attached glycan apparently has only a very minor impact on protein thermal stability (Shental-Bechor and Levy, 2009) which makes naturally occurring N-Glycans an ideal linker for the conjugation of functional compounds— even if such compounds have a high molecular mass. In line with this, U.S. Pat. No. 7,138,371 and United States Patent Application 2010/0048456 disclose methods for conjugating polypeptides via the protein linked glycostructure to polyethylene glycol. Both of these documents as well as related applications and patents still did not solve the problem that leads to coupling heterogeneity.

Thus, there is still a need for homogenous and stable protein-pharmaceutically active compound-conjugates, wherein the pharmaceutically active compounds are coupled via an exactly defined moiety to the proteins. Particularly, site-directed coupling of pharmaceutically active compounds to proteins via a predetermined sugar attachment site is desirable. There is also still a need for cells for producing proteins which comprise such an exactly defined coupling moiety in high yields and which, thus, allow homogeneous and efficient coupling of pharmaceutically active compounds in a high degree, methods for producing such proteins using said cells, and methods for producing conjugates comprising such proteins and pharmaceutically active compounds.

The inventors of the present invention surprisingly found that homogenous, efficient, stable and site-directed coupling of pharmaceutically active compounds to molecules such as lipids or proteins can be achieved via an artificial core fucose analogue introduced into the glycostructure of said molecules. They also surprisingly found that homogenous, efficient, stable and site-directed coupling of pharmaceutically active compounds to proteins, e.g. glycoproteins, can be achieved via an artificial fucose molecule linked to a protein-O-fucosylation site incorporated in or attached to the amino acid sequence of said proteins. They particularly provide cells and methods which allow the production of said molecules, e.g. proteins or lipids, and conjugates between said molecules, e.g. proteins or lipids, and a pharmaceutically active compound in high yields. The produced conjugates are thermally stable and homogenous. The molecule can be a glycoengineered protein, a therapeutic protein, an antibody, a vaccine component, even a protein comprised in the envelope of an enveloped virus. The advantageous unifying concept is that the molecule, e.g. protein or lipid, is produced by a cell that is engineered for impaired innate fucosylation to its proteome so that exogenously added fucose is preferentially incorporated at a specific site, and that this exogenously added fucose is chemically activated so that further pharmaceutically active compounds can be selectively and covalently attached to said molecule. The added pharmaceutically active compound can be a compound that enhances or transforms the properties of the molecule, e.g. protein such as an anitbody or lipid, for example, it can increase cytotoxicity, increase biological half life, induce targeting of the molecule to specific tissues, protect against degradation or aggregation, induce or enhance innate or adaptive immunity, or increase or decrease infectivity of live viruses.

In one or more aspects, embodiments, preferred embodiments or more preferred embodiments of the present invention described below, the particular fucose analogue comprising molecules, e.g. proteins or lipids, or the particular fucose analogue-linked conjugates with site-specific attachment of a molecule, e.g. protein or lipid, and a pharmaceutically active compound (e.g. immunoconjugates) may have one or more of the following advantages:

(I) A fucose analogue bound to the fucosylation site of the chitobiose core of proteins allows the coupling of a limited and defined number of pharmaceutically active compounds and, thus, enables the production of homogenously coupled conjugates. This positively influences product yield, lot consistency, therapeutic efficacy, and product comparability.

(II) The fucose analogue has only a very minor impact on overall protein thermal stability. Thus, therapeutic efficacy by avoiding inactive compounds can be increased.

(III) The artificial introduction of further defined N-glycosylation sites achieved due to the introduction of a single point mutation in the vicinity of a suitable asparagine residue, allows further site specific coupling of additional pharmaceutical compounds per protein molecule.

(IV) To link the pharmaceutically active compound via a fucose analogue which is bound to the fucosylation site of the chitobiose core is advantageous as the distal part of a glycan is accessible to enzymatic degradation and hence coupling at those distal sites would result in instability of the conjugate. Chemical homogeneity and coupling stability of the conjugate is achieved by direct coupling of a pharmaceutically active compound to a fucose analogue monosaccharide bound at a defined position in the polypeptide chain (C glycan or O-glycan) or in the glycan structure. In case of an N-linked glycan, the core fucose, i.e. the particular fucose residue alpha-1,6-linked to the reducing end of the first N-acetylglucosamine residue of the chitobiose core of an N-glycan constitutes the shortest possible, defined and homogenous glyco-linker for such an N-linked-glycoconjugate.

(V) The fucose analogue can be added to the culture medium. It is then taken up and further metabolized by conventional cells. However, the efficiency of the fucose de novo synthetic pathway starting from the abundant monosaccharide mannose (that itself is part of N glycans) provides 90% of the GDP fucose pool even in the presence of exogenous fucose and prevents efficient incorporation of fucose analogue into glycoproteins and inevitably results in a heterogeneous mixture of glycoproteins that are enabled for fucose-directed coupling to a low degree. Surprisingly, the inventors of the present invention found that cells with an interrupted biosynthesis pathway for fucose grown in a cell culture medium containing specific coupling-enabled fucose analogues efficiently incorporate the fucose analogue into glycoproteins produced in said cells. This results in a homogenous mixture of glycoproteins that are enabled for fucose-directed coupling to a high degree. In addition, the inventors found similar growth and performance parameters as the unmodified parental cell line grown in a medium not spiked with a coupling-enabled fucose analogue.

(VI) Unlike other coupling technologies that rely on incorporation of coupling-enabled artificial amino acids or sugars into a produced protein, the technology described herein does not suffer from the associated process yield decline typically seen for such modified proteins. In particular, the inventors did not observe a block of core-fucosylation as it was described in previous patent applications concerning fucose alkyne or azido-fucose. In contrast thereto, the inventors observed an unexpected and efficient incorporation of azido-fucose.

(VII) The covalent chemical bond between the protein bound fucose analogue and the conjugated pharmaceutically active compound is stable, not sensitive to mild reduction and therefore mitigates the risk of unwanted systemic release of the conjugated moiety.

(VIII) Apart from antibody drug conjugates that kill target cells via the attached toxin cell mediated cytotoxicity, antibody dependent cellular cytotoxicity (ADCC) is the dominating mechanism of action of therapeutic antibodies, e.g. IgG1-type therapeutic antibodies. Such antibody molecules should either allow coupling of a toxin or be equipped for efficient ADCC. It is further desirable that a drug conjugated molecule is disabled for ADCC to avoid toxicity directed towards effector cells. It is, thus, desirable for toxin-linked conjugates to combine both action principles in a single drug in particular if an antibody coupling efficiency does not reach 100%. The present invention may provide a solution. Linking the drug via a fucose analogue will obliterate effector functions such as ADCC and uncoupled antibodies within an antibody composition produced in the cells disclosed herein will lack fucose and therefore provides enhanced ADCC.

(IX) It is particularly advantageous if a fucose analogue which is directly linked to the polypeptide chain of a protein enables chemically homogenous coupling between said protein and a pharmaceutically active compound. This is achieved without modification of a protein that naturally contains a single or several protein-O-fucosylation sites. For proteins that do not contain protein-O-fucosylation sites or contain less sites than desired, the inventors of the present invention found the incorporation of an EGF-like repeat, representing such site, is very eligible.

SUMMARY OF THE INVENTION

In a first aspect, the present invention relates to a eukaryotic cell for producing a molecule comprising a fucose analogue, wherein
(i) in said cell the GDP-L-fucose synthesis pathway originating from GDP-D-mannose is blocked, and
(ii) said cell comprises a GDP-L-fucose analogue.

In a second aspect, the present invention relates to a method for producing a molecule which comprises a fucose analogue comprising the steps of:
(i) providing a eukaryotic cell according to the first aspect, and
(ii) isolating the molecule comprising a fucose analogue from the cell in i).

In a third aspect, the present invention relates to a molecule comprising a fucose analogue obtainable by the method of the second aspect.

In a fourth aspect, the present invention relates to a method for producing a conjugate comprising a molecule which comprises a fucose analogue and a pharmaceutically active compound comprising the steps of:
(i) carrying out the method of the second aspect, and
(ii) covalently coupling a pharmaceutically active compound via the fucose analogue to the molecule comprising said fucose analogue.

In a fifth aspect, the present invention relates to a conjugate comprising a molecule which comprises a fucose analogue and a pharmaceutically active compound obtainable by the method of the fourth aspect.

In a sixth aspect, the present invention relates to a conjugate which comprises a protein or polypeptide comprising one or more of the following structures:

—NG-cF*—Y$_o$—C, wherein each is attached to an N-glycosylation site comprised in said protein or polypeptide,
NG is an N-linked glycomoiety of said protein or polypeptide,
cF* is a core fucose analogue,
Y is a spacer unit, wherein o is an integer of 0 or 1, and
C is a pharmaceutically active compound.

In a seventh aspect, the present invention relates to a conjugate which comprises a protein or polypeptide comprising one or more EGF-like repeats comprising a serine and/or threonine residue to which the following structure:

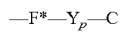

is attached, wherein

F* is a fucose analogue moiety directly O-linked to said serine and/or threonine residue, Y is a spacer unit, wherein p is an integer of 0 or 1, and C is a pharmaceutically active compound.

This summary of the invention does not describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. The focus of the invention rests on a method for efficient production of site-specific fucose-linked glycoprotein conjugates. However, the particular features of the unique type of products attainable by this method are also of importance and specifically considered in example 1.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

In the context of the present invention, the term "peptide" refers to a short polymer of amino acids linked by peptide bonds. It has the same peptide bonds as those in proteins, but is commonly shorter in length. The shortest peptide is a dipeptide, consisting of two amino acids joined by a single peptide bond. There can also be a tripeptide, tetrapeptide, pentapeptide, etc. A peptide is preferably one that is less than about 30 amino acids long and more preferably less than about 20 amino acids long.

The term "polypeptide", as used herein, refers to a part of a protein which is composed of a single linear chain of amino acids bonded together by peptide bonds. Said chain of amino acids is preferably more than about 30 amino acids long or longer than 30 amino acids.

The term "protein", as used herein, refers to a protein which comprises one or more polypeptides that resume a secondary and tertiary structure and additionally refers to a protein that is made up of several amino acid chains, i.e. several subunits, forming quaternary structures. The protein has sometimes non-peptide groups attached, which can be called prosthetic groups or cofactors.

The term "polypeptide fragment", as used in the context of the present invention, refers to a polypeptide that has a deletion, e.g. an amino-terminal deletion, and/or a carboxy-terminal deletion, and/or an internally deletion compared to a full-length polypeptide.

In the context of the present invention, the term "fusion protein" refers to a protein comprising a polypeptide or polypeptide fragment coupled to heterologous amino acid sequences. Fusion proteins are useful because they can be constructed to contain two or more desired functional elements from two or more different proteins.

The terms "antibody", "immunoglobulin", "Ig" and "Ig molecule" are used interchangeably in the context of the present invention. The CH2 domain of each heavy chain contains a single site for N-linked glycosylation at an asparagine residue linking an N-glycan to the antibody molecule, usually at residue Asn-297 (Kabat et al., Sequence of proteins of immunological interest, Fifth Ed., U.S. Department of Health and Human Services, NIH Publication No. 91-3242). Included within the scope of the term are classes of Igs, namely, IgG, IgA, IgE, IgM, and IgD. Also included within the scope of the terms are the subtypes of IgGs, namely, IgG1, IgG2, IgG3 and IgG4. The terms are used in their broadest sense and include monoclonal antibodies (including full length monoclonal antibodies), polyclonal antibodies, single chain antibodies, and multispecific antibodies (e.g. bispecific antibodies).

The term "antibody fragment", as used in the context of the present invention, refers to a fragment of an antibody that contains at least the portion of the CH2 domain of the heavy chain immunoglobulin constant region which comprises an N-linked glycosylation site of the CH2 domain. It may also be capable of specific binding to an antigen, i.e. chains of at least one $V_L$ and/or $V_H$-chain or binding part thereof.

The terms "Fc domain" and "Fc region", as used herein, refer to a C-terminal portion of an antibody heavy chain that interacts with cell surface receptors called Fc receptors and some proteins of the complement system. This property allows antibodies to activate the immune system.

In the context of the present invention, the term "glycoprotein" refers to proteins that contain oligosaccharide chains (glycans) covalently attached to their polypeptide side-chains. The carbohydrate is attached to the protein in a co-translational or posttranslational modification. This process is known as glycosylation such as N-glycosylation or O-glycosylation.

"N-glycosylation" means the addition of sugar chains which to the amide nitrogen on the side chain of asparagine. "O-glycosylation" means the addition of sugar chains on the hydroxyl oxygen on the side chain of hydroxylysine, hydroxyproline, serine, or threonine.

The term "glycolipid" as used in the context of the present invention refers to carbohydrate-attached lipids. They occur where a carbohydrate chain is associated with phospholipids on the exoplasmic surface of the cell membrane. The carbohydrates are found on the outer surface of all eukaryotic cell membranes. The carbohydrate structure of the glycolipid is controlled by the glycosyltransferases that add the lipids and glycosylhydrolases that modify the glycan after addition. Glycolipids also occur on the surface of enveloped viruses including those used as attenuated life vaccines.

The terms "glycan" or "glycomoiety" are used interchangeably in the context of the present invention to refer to a polysaccharide or oligosaccharide. The term "oligosaccharide" means a saccharide polymer containing a small number (typically three to ten) of component sugars, also known as simple sugars or monosaccharides. The term "polysaccharide" means a polymeric carbohydrate structure, formed of repeating units (either mono- or disaccharides, typically>10) joined together by glycosidic bonds. Glycans can be found attached to proteins as in glycoproteins or attached to lipids as in glycolipids. The terms encompass N-glycans, such as high mannose type N-glycans, complex type N-glycans or hybrid type N-glycans, O-glycans or In the context of the present invention, the following monosaccharides are abbreviated as follows: Glucos=Glc, Galactose=Gal, Mannose=Man, Fucose=Fuc or F, N-acetylgalactosamine=GalNAc, or N-acetylglucosamine=GlcNAc, Fucose analogue=Fuc* or F*.

An "N-glycan" means an N-linked polysaccharide or oligosaccharide. An N-linked oligosaccharide is for example one that is or was attached by an N-acetylglucosamine residue linked to the amide nitrogen of an asparagine residue in a protein. The predominant sugars found on N-glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues in the Golgi apparatus for N-linked glycoproteins. N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ core structure which is also referred to as the "trimannose core", the "pentasaccharide core" or the "paucimannose core". N-glycans are classified according to their branched constituents (e.g., high mannose, complex or hybrid).

A "high mannose type N-glycan" means an N-linked polysaccharide or oligosaccharide which has five mannose residues ($Man_5$), or more mannose residues (e.g. $Man_6$, $Man_7$, or $Man_8$).

A "complex type N-glycan" means a N-linked polysaccharide or oligosaccharide which typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex type N-glycans in the context of the present invention may contain zero (G0), one (G1), or two (G2) galactoses as well as one fucose attached to the first GlcNAc on the reducing end (denoted as G0F, G1F, G2F, respectively).

A "hybrid type N-glycan" means a N-linked polysaccharide or oligosaccharide which has at least one GlcNAc on the terminal of the 1,3 mannose arm of the trimannose core and zero or more mannoses on the 1,6 mannose arm of the trimannose core.

The abbreviations used in the context of the present invention to describe the glycostructures are defined as follows:

core=$Man_3 GlcNAc_2$
G0=$GlcNAc_2 Man_3 GlcNAc_2$
G0-GlcNAc=G0-structure missing one GlcNAc (i.e. GlcNAc $Man_3 GlcNAc_2$)
G1=G0-structure containing one additional Galactose residue
  (i.e. Gal $GlcNAc_2 Man_3 GlcNAc_2$)
G2=G0-structure containing two additional Galactose residues (i.e. $Gab GlcNAc_2 Man_3 GlcNAc_2$)
G0F=G0-Structure containing an additional fucose-residue which is connected to the first GlcNAc-residue of the pentasaccharide core (i.e. $GlcNAc_2 Man_3 GlcNAc_2 Fuc$)
G0F-GlcNAc=G0-GlcNAc-structure containing an additional fucose-residue which is connected to the first GlcNAc-residue of the pentasaccharide core (i.e. GlcNAc $Man_3 GlcNAc_2 Fuc$)
G1F=G1-structure containing an additional fucose-residue which is connected to the first GlcNAc-residue of the pentasaccharide core (i.e. Gal $GlcNAc_2 Man_3 GlcNAc_2 Fuc$)
G2F=G2-structure containing an additional fucose-residue which is connected to the first GlcNAc-residue of the pentasaccharide core (i.e. $Gal_2 GlcNAc_2 Man_3 GlcNAc_2 Fuc$)
Man4=core-structure containing one additional Mannose residue
  (i.e. Man $Man_3 GlcNAc_2$)
Man5=core-structure containing two additional Mannose residues
  (i.e. $Man_2 Man_3 GlcNAc_2$)
Man6=core-structure containing three additional Mannose residues
  (i.e. $Man_3 Man_3 GlcNAc_2$)
Man7=core-structure containing four additional Mannose residues
  (i.e. $Man_4 Man_3 GlcNAc_2$)
Man8=(core-structure containing five additional Mannose residues
  (i.e. $Man_5 Man_3 GlcNAc_2$).

To exemplarily describe glycostructures comprising a fucose analogue, the above mentioned F (fucose) can simply be replaced by F* (fucose analogue). For example, in case where an antibody with an N-glycan structure comprising a core Fucose analogue (cF*) is produced with the methods of the present invention.

An "O-glycan" means an O-linked polysaccharide or oligosaccharide. O-Linked glycans are usually attached to the peptide chain through serine or threonine residues. O-Linked glycosylation is a true post-translational event which occurs in the Golgi apparatus and which does not require a consensus sequence and no oligosaccharide precursor is required for protein transfer. The most common type of O-linked glycans contain an initial GalNAc residue (or Tn epitope), these are commonly referred to as mucin-type glycans. Other O-linked glycans include glucosamine, xylose, galactose, fucose, or mannose as the initial sugar bound to the Ser/Thr residues. O-Linked glycoproteins are usually large proteins (>200 kDa) that are commonly biantennary with comparatively less branching than N-glycans.

Animal and human cells have fucosyltransferases that add a fucose residue to the GlcNAc residue at the reducing end of the N-glycans on a protein or to other nascent glycostructures on glycolipids. Fucosylation of protein- or lipid-bound glycomoieties requires a nucleotide sugar, GDP-L-fucose, as a donor and also the presence of particular fucosyl transferases, which transfer the fucosyl residue from the donor to the acceptor molecule (Becker and Lowe, 1999). In eukaryotic cells, e.g. vertebrate cells, GDP-L-fucose can be synthesized via two different pathways, either by the more prominent fucose de novo pathway or by the minor salvage pathway (Becker and Lowe, 1999). The salvage Pathway or "scavenger" pathway is a minor source of GDP-L-fucose (circa 10%) which can easily be blocked by omission of free fucose and fucosylated glycoproteins from the culture medium. The salvage pathway starts from extracellular fucose which can be transported into the cytosolic compartment via fucose-specific plasma membrane transporters. Alternatively, fucose cleaved from endocytosed glycoproteins can enter the cytosol. Cytosolic L-fucose is phosphorylated by fucokinase to fucose-1-phosphate and then converted by GDP-Fucose Pyrophosphorylase to GDP-L-fucose (FIG. 1, right hand panel). Cell culture experiments suggest that the salvage pathway makes a relatively minor contribution to the cytosolic GDP-L-fucose pools (Becker and Lowe, 1999).

The more prominent fucose de novo pathway starts from GDP-D-mannose and consists of a GDP-mannose dehydratase (GMD) and GDP-keto-deoxy-mannose-epimerase/GDP-keto-deoxy-galactose-reductase (GMER, also known as Fx in humans), both located in the cytoplasm, which in concert converts GDP-mannose to GDP-L-fucose (FIG. 1, left hand panel). Later, GDP-L-fucose is transported into the Golgi via a GDP-fucose transporter located in the membrane of the Golgi apparatus. Once GDP-L-fucose has entered the Golgi luminal compartment, fucosyltransferases can covalently link GDP-L-fucose to nascent glycomoieties within the Golgi. In particular, Fucosyltransferase (Fut8) transfers the fucose residue by means of an 1,6-linkage to the 6 position of the GlcNAc residue at the reducing end of the N-glycan.

As mentioned above, coupling of pharmaceutically active compounds to proteins, e.g. antibodies, in a stable, specific, homogenous and efficient manner is highly desirable in the medical field. Particularly, site-directed coupling of conjugates via predetermined attachment sites is desirable.

The inventors of the present invention surprisingly determined that homogenous, efficient, stable and site-directed coupling of pharmaceutically active compounds to molecules such as lipids or proteins (e.g. glycoproteins such as antibodies) can be achieved via an artificial core fucose analogue introduced into the glycostructure of said molecules. They also surprisingly found that homogenous, efficient, stable and site-directed coupling of pharmaceutically active compounds to proteins (e.g. glycoproteins such as antibodies) can be achieved via an artificial fucose analogue linked to a protein-O-fucosylation site incorporated in or attached to the amino acid sequence of said proteins. Moreover, said fucose analogues have the particular advantage that they allow, in contrast to natural fucose molecules, the specific coupling of pharmaceutically active compounds to molecules such as proteins or lipids, to which they are attached.

In addition, the inventors of the present invention surprisingly found that in a cell, wherein the GDP-L-fucose synthesis pathway originating from GDP-D-mannose (de novo pathway) is blocked, molecules comprising a fucose analogue on its glycomoieties or amino acids instead of natural fucose can be produced in high yields. Reason for this is that any competitive incorporation of natural fucose is completely abolished in such a gycoengineered cell. The use of fucose-free medium and of a cell with obstructed fucose de-novo synthesis pathway leaves the fucose analogue as the exclusive substrate for fucosyltransferases present in such a cell. Moreover, since the natural GDP-fucose, the product of the fucose de novo synthesis pathway, is a competitive inhibitor of the salvage pathway fucose kinase, a block of the de novo synthesis additionally speeds up salvage pathway efficiency and, thus, the production of the metabolized GDP form of the fucose analogue which can be incorporated into molecules present in said cell, e.g. into nascent glycostructures of proteins. Accordingly, with a cell having an abolished fucose de novo synthesis pathway and comprising a fucose analogue, molecules such as proteins or lipids bearing a fucose analogue on its surface can be produced in a stoichiometrically efficient manner.

Thus, in a first aspect, the present invention provides a eukaryotic cell for producing a molecule comprising a fucose analogue, wherein
(i) in said cell the GDP-L-fucose synthesis pathway originating from GDP-D-mannose is blocked, and
(ii) said cell comprises a GDP-L-fucose analogue.

The term "a molecule which comprises a fucose analogue", as used in the context of the present invention, refers to any compound which upon production in the eukaryotic cell of the present invention, preferably vertebrate cell, capable of adding a fucose analogue (instead of a natural fucose) to said compound, e.g. to its glycomoieties or amino acids, i.e. with an ability to add a fucose analogue (instead of a natural fucose) to said compound, e.g. to its glycomoieties or amino acids, comprises at least one fucose analogue, e.g. on its glycomoieties or amino acids. Such molecules comprise at least one or more sequence motifs recognized by a glycan transferring enzyme, e.g. comprising an Asp, Ser or Thr residue, preferably a tripeptide sequence Asn-X-Ser/Thr, wherein X is any amino acid except Pro. The glycan transferring enzyme comprised in the cell of the present invention is able to attach, if natural fucose is not available, also a fucose analogue to said molecules, e.g. to their glycomoieties or amino acids. In other words, a molecule which would naturally comprise a fucose molecule, e.g. on its glycomoieties or amino acids, after production in an unaltered cell, comprises upon production in the cell of the present invention a fucose analogue, e.g. on its glycomoieties or amino acids. A cell that produces molecules comprising amino acids or glycomoieties with natural fucose is, for example, a CHO, AGE1.HN, AGE1.CR, AGE1.CR.PIX, or AGE1.CS cell.

The skilled person can easily determine experimentally the presence of a fucose analogue and/or the amount of a fucose analogue on the glycomoieties of a particular molecule, e.g. an antibody molecule, by (i) cultivating cells of the present invention under conditions wherein the molecule of interest is produced, (ii) isolating said molecule from said cells and (iii) analysing the sugar chain structure of said molecule with respect to the fucose residues attached to its glycomoieties and determining the type of fucose residues and/or calculating the mean value of fucose residues present on the sugar chain structure of said molecule, and (iv) comparing the result with the result of the same molecule, e.g. an antibody molecule, produced in the same cells, wherein the molecule is produced with a fucose analogue-free pattern. Preferably, the cells used in the two experiments are identical but for the difference that one cell (the cell of the present invention) is cultured in the presence of a fucose analogue. Preferably both cells are cultivated under the identical culture conditions to exclude variations in fucosylation that may be due to differences in culture conditions. The same methodology can be used to determine experimentally the presence of a fucose analogue and/or the amount of a fucose analogue on the amino acid structure of a particular molecule, e.g. an antibody molecule.

The sugar chain structure in a molecule, e.g. antibody molecule, can simply be analyzed by the two dimensional sugar chain mapping method (Anal. Biochem., 171, 73 (1988), Biochemical Experimentation Methods 23—Methods for Studying Glycoprotein Sugar Chains (Japan Scientific Societies Press) edited by Reiko Takahashi (1989)). The structure deduced by the two dimensional sugar chain mapping method can be determined by carrying out mass spectrometry such as MALDI (Matrix Assisted Laser Desorption/Ionisation)-TOF-MS of each sugar chain.

The term that the GDP-L-fucose synthesis pathway originating from GDP-D-mannose (de novo pathway) is "blocked", as used herein, means that said pathway is blocked by at least 50%, preferably by at least 60% or 70%, more preferably by at least 80% or 90%, and most preferably by at least 95% or 100%, e.g. by at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. The skilled person can easily determine experimentally the grade of de novo pathway blocking by determining the level of GDP-L-fucose produced in a cell wherein the GDP-L-fucose synthesis pathway originating from GDP-D-mannose (de novo pathway) is blocked/interrupted and comparing it with the level of GDP-L-fucose produced in a cell wherein the GDP-L-fucose synthesis pathway originating from GDP-D-mannose (de novo pathway) is not blocked/interrupted. In this context, for example, a reduction of the level of GDP-L-fucose by 50% compared to the level of GDP-L-fucose determined in a control cell means a blocking of the de novo pathway by 50% and a reduction of the level of GDP-L-fucose by 100% compared to the level of GDP-L-fucose determined in a control cell means a blocking of the de novo pathway by 100%. Preferably, the cells used in the two experiments are identical but for the difference that one cell (the cell of the present invention) comprises, for example, at least one enzyme which uses GDP-6-deoxy-D-lyxo-4-hexylose as a substrate, wherein the enzyme does not catalyze the reaction which converts GDP-6-deoxy-D-lyxo-4-hexylose into GDP-L-fucose in order to block the de novo pathway. Preferably both cells are cultivated under the identical culture conditions (e.g. culture medium or culturing time) to exclude variations in fucosylation that may be due to differences in culture conditions. It is particularly preferred that both cells are cultivated in the absence of an external fucose source to eliminate the influence of the salvage pathway on the amount of GDP-L-fucose produced in said cells. In addition, the skilled person knows how to determine the level of GDP-L-fucose to calculate the level/grade of blocking of the de novo pathway.

Blocking of the GDP-L-fucose synthesis pathway originating from GDP-D-mannose (de novo pathway) may be achieved in any way and at any step(s) (e.g. at one or more steps) in the de novo pathway provided that a reduced level of GDP-L-fucose (at least 50%), preferably no GDP-L-fucose, is produced from GDP-D-mannose in said cell (see above). This may be achieved due to (i) the mutation of enzyme(s) involved in said pathway so that their enzymatic activity is reduced or abolished, (ii) the knock-out or partial knock-out of gene(s) or promoter region(s) regulating said gene(s) so that no enzymatically active enzyme(s) involved in said pathway are produced or so that enzyme(s) with a reduced enzymatic activity involved in said pathway are produced, and/or (iii) the knock-down or partial knock-down of the mRNA(s) encoding said enzymes(s) with miRNA technology so that no so that no enzymatically active enzyme(s) involved in said pathway are produced or so that enzyme(s) with a reduced enzymatic activity involved in said pathway are produced (see FIG. 1, left hand panel). Said enzyme(s) could be, for example GDP-mannose dehydratase (GMD) and/or GDP-Fucose synthetase (GFS).

Fucosylation of molecules, e.g. proteins or lipids, comprising glycomoieties in eukaryotic cells (e.g. vertebrate cells) requires a nucleotide sugar, GDP-L-fucose, as a donor and also the presence of particular fucosyltransferases, which transfer the fucosyl residue from the donor to the acceptor molecule. As mentioned above, in eukaryotic cells (e.g. vertebrate cells) GDP-L-fucose can be synthesized via two different pathways, either by the more prominent fucose de novo pathway or by the minor salvage pathway.

In a preferred embodiment, the GDP-L-fucose synthesis pathway originating from GDP-D-mannose (de novo pathway) is blocked, preferably to 80%, more preferably to 90% and most preferably to 95% or 100%, due to the presence of an enzyme (deflecting enzyme) in a eukaryotic cell (e.g. a vertebrate cell) which uses GDP-6-deoxy-D-lyxo-4-hexylose as a substrate, but which does not catalyse the reaction which converts GDP-6-deoxy-D-lyxo-4-hexylose into GDP-L-fucose. In this respect, it should be noted that the term "GDP-6-deoxy-D-lyxo-4-hexylose" is synonym with the term "GDP-4-keto-6-deoxy-D-mannose". Both terms are used interchangeably herein.

Said enzyme present in the eukaryotic cell, e.g. vertebrate cell, can be any enzyme which uses GDP-6-deoxy-D-lyxo-4-hexylose as a substrate under the proviso that said enzyme does not catalyze the reaction which converts GDP-6-deoxy-D-lyxo-4-hexylose into GDP-L-fucose. Rather said enzyme converts GDP-6-deoxy-D-lyxo-4-hexylose into a product that can no longer be utilized for GDP-L-fucose synthesis in a eukaryotic cell, e.g. vertebrate cell. The enzyme which is preferably comprised in the eukaryotic cell, e.g. vertebrate cell, is an enzyme which is normally not present in said cell, i.e. a heterologous or artificial enzyme, e.g. an enzyme from an organism of another kingdom, such as from prokaryotes, preferably bacteria. Alternatively said enzyme can also be an enzyme which is normally present in a eukaryotic cell, e.g. vertebrate cell, but which does not covert the substrate GDP-6-deoxy-D-lyxo-4-hexylose into GDP-L-fucose but rather into a different product, e.g. due to the presence of mutations.

The enzyme, which is preferably present in the eukaryotic cell, e.g. vertebrate cell, may be introduced into said cell, for example, via protein microinjection, protein electroporation or protein lipofection. It is also possible to introduce the nucleic acid sequence encoding the enzyme, preferably integrated in an expression vector, into the vertebrate cell, for example via DNA microinjection, DNA electroporation or DNA lipofection, which is subsequently transcribed and translated into the respective protein in the eukaryotic cell, e.g. vertebrate cell. The person skilled in the art is well informed about molecular biological techniques, such as microinjection, electroporation or lipofection, for introducing proteins or nucleic acid sequences encoding proteins into a eukaryotic cell, e.g. vertebrate cell, and knows how to perform these techniques.

It is preferred that two or more enzymes, i.e. 2, 3, 4, 5, 6 or 7, which use GDP-6-deoxy-D-lyxo-4-hexylose as a substrate and which do not catalyze the conversion of GDP-6-deoxy-D-lyxo-4-hexylose into GDP-L-fucose are present in a eukaryotic cell, e.g. vertebrate cell, to effectively block the fucose de novo pathway in said cell.

Preferably, the enzyme which uses GDP-6-deoxy-D-lyxo-4-hexylose as a substrate is selected from the group consisting of GDP-6-deoxy-D-lyxo-4-hexylose reductase (synonym with GDP-4-keto-6-deoxy-D-mannose reductase, abbreviated RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), preferably GDP-4-keto-6-deoxymannose-3-dehydratase (ColD) in combination with GDP-L-colitose synthase (ColC), and variants thereof, preferably the enzyme is from bacteria or derived from such a bacterial enzyme. More preferably, the enzyme which uses GDP-6-deoxy-D-lyxo-4-hexylose as a substrate is a GDP-6-deoxy-D-lyxo-4-hexylose reductase (RMD), GDP-Fucose synthetase Cys109Ser-(GFS-Cys109Ser) mutant, and/or a GDP-perosamine synthetase (Per).

GDP-6-deoxy-D-lyxo-4-hexylose reductase (RMD) reduces the substrate GDP-6-deoxy-D-lyxo-4-hexylose to GDP-D-rhamnose. GDP-D-rhamnose is a nucleotide sugar donor for D-rhamnosylation in bacteria and does not occur in eukaryotes, e.g. vertebrates. Eukaryotic cells, e.g. vertebrate cells, also lack specific rhamnosyltransferases so that GDP-D-rhamnose can not be incorporated into nascent glycostructures of glycoproteins or glycolipids within eukaryotic cells, e.g. vertebrate cells.

The enzyme GDP-6-deoxy-D-talose synthetase (GTS) reduces the substrate GDP-6-deoxy-D-lyxo-4-hexylose to GDP-deoxy-D-talose. GDP-deoxy-D-talose is a nucleotide sugar donor for 6-deoxy-D-talosylation in bacteria and does not occur in eukaryotes, e.g. vertebrates. Eukaryotic cells, e.g. vertebrate cells, also lack specific deoxytalosyltransferases so that GDP-deoxy-D-talose can not be incorporated into nascent glycostructures within vertebrate cells.

Further, the enzyme GDP-perosamine synthetase (Per) reduces and transaminates the substrate GDP-6-deoxy-D-lyxo-4-hexylose to GDP-D-perosamine. GDP-D-perosamine is a nucleotide sugar donor for perosaminylation in bacteria, e.g. E. coli. GDP-D-perosamine is normally not present in eukaryotic cells, e.g. vertebrate cells. Eukaryotic cells, e.g. vertebrate cells also lack specific perosaminyltransferases so that GDP-D-perosamine can not be attached to nascent glycostructures within eukaryotic cells, e.g. vertebrate cells.

Therefore, the heterologous enzymes GTS and/or Per (i) deplete the substrate GDP-6-deoxy-D-lyxo-4-hexylose in the eukaryotic cell, e.g. vertebrate cell, and (ii) lead to the synthesis of artificial products (i.e. GDP-deoxy-D-talose in the case of GTS and GDP-D-perosamine in the case of Per) which can no longer be utilized for GDP-L-fucose synthesis.

Accordingly, a molecule which would usually comprise (natural) fucose on its glycomoieties and/or amino acids in a eukaryotic cell, wherein the de novo pathway is not blocked, and which is produced in the eukaryotic cell of the present invention, e.g. in a eukaryotic cell comprising GTS and/or Per and a fucose analogue, lacks (natural) fucose on its glycomoieties and/or amino acids, but comprises instead of (natural) fucose a fucose analogue on its glycomoieties and/or amino acids.

The enzyme GDP-4-keto-6-deoxymannose-3-dehydratase (ColD) uses the substrate GDP-6-deoxy-D-lyxo-4-hexylose and converts it into GDP-4-keto-3,6-dideoxy-D-mannose. As the intermediate GDP-4-keto-3,6-dideoxy-D-mannose can be instable in eukaryotic cells, e.g. vertebrate cells, ColD is preferably used in combination with the enzyme GDP-L-colitose synthase (ColC). The enzyme ColC belongs to the class of GDP-4-dehydro-6-deoxy-D-mannose epimerases/reductases. The enzyme ColC further converts the intermediate GDP-4-keto-3,6-dideoxy-D-mannose into the stabile end-product GDP-L-colitose. Both products can not be incorporated into nascent glycostructures within eukaryotic cells, e.g. vertebrate cells, as said cells lack the respective glycosyltransferase to transfer GDP-4-keto-3,6-dideoxy-D-mannose and/or GDP-L-colitose to the glycomoieties of molecules present in said cells. Thus, it is preferred that ColD is present in the eukaryotic cell, e.g. vertebrate cell, in combination with ColC.

The enzyme GDP-Fucose synthetase (GFS) (also known as GDP-4-keto-6-deoxy-D-mannose epimerase/reductase, GMER) converts GDP-4-keto-6-deoxy-D-mannose into GDP-L-fucose in eukaryotic cells, e.g. vertebrate cells. The GFS reaction involves epimerizations at both C-3" and C-5" followed by an NADPH-dependent reduction of the carbonyl at C-4. An active site mutant, preferably GFS-Cys109Ser, is used in the present invention, which converts GDP-4-keto-6-deoxy-D-mannose into a product different from GDP-L-fucose, namely GDP-6-deoxy-D-altrose (see Lau S. T. B., Tanner, M. E. 2008. Mechanism and active site residues of GDP-Fucose Synthase, Journal of the American Chemical Society, Vol. 130, No. 51, pp. 17593-17602).

Preferably, two or more enzymes, i.e. 2, 3, 4, 5, 6, or 7, selected from the group consisting of GDP-6-deoxy-D-lyxo-4-hexylose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), preferably GDP-4-keto-6-deoxymannose-3-dehydratase (ColD) in combination with GDP-L-colitose synthase (ColC), and variants thereof are present in the eukaryotic cell, e.g. vertebrate cell.

A RMD, Per, GTS, GFS-Cys109Ser, ColD, or ColC enzyme variant which is preferred in the present invention differs from the RMD, Per, GTS, GFS-Cys109Ser, ColD, or ColC enzyme from which it is derived by up to 150 (i.e. up to 1, 2, 3, 4, 5, 6, 7, 8, 9, 10, 11, 12, 13, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, or 150) amino acid changes in the amino acid sequence (i.e. exchanges, insertions, deletions, N-terminal truncations and/or C-terminal truncations). The amino acid exchanges may be conservative or non-conservative. A RMD, Per, GTS, GFS-Cys109Ser, ColD, or ColC enzyme variant, which is preferred in the present invention can alternatively or additionally be characterised by a certain degree of sequence identity to the RMD, Per, GTS, GFS-Cys109Ser, ColD, or ColC enzyme from which it is derived. Thus, the RMD, Per, GTS, GFS-Cys109Ser, ColD, or ColC enzyme variants, which are preferred in the present invention have a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference RMD, Per, GTS, GFS-Cys109Ser, ColD, or ColC enzyme. Preferably, the sequence identity is over a continuous stretch of 40, 45, 50, 60, 70, 80, 90, 100, 150, 200, 250, 300 or more amino acids, preferably over the whole length of the respective reference RMD, Per, GTS, GFS-Cys109Ser, ColD, or ColC enzyme. It is particularly preferred that the sequence identity is at least 80% over the whole length, is at least 85% over the whole length, is at least 90% over the whole length, is at least 95% over the whole length, is at least 98% over the whole length, or is at least 99.5% over the whole length of the respective reference RMD, Per, GTS, GFS-Cys109Ser, ColD, or ColC enzyme. It is also particularly preferred that the sequence identity is at least 80% over at least 200 or 250 amino acids, is at least 85% over at least 200 or 250 amino acids, is at least 90% over at least 200 or 250 amino acids, is at least 95% over at least 200 or 250 amino acids, is at least 98% over at least 200 or 250 amino acids, or is at least 99.5% over at least 200 or 250 amino acids of the respective reference RMD, Per, GTS, GFS-Cys109Ser, ColD, or ColC enzyme.

A fragment (or deletion variant) of the RMD, Per, GTS, GFS-Cys109Ser, ColD, or ColC enzyme has preferably a deletion of up to 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, or 150 amino acids at its N-terminus and/or at its C-terminus and/or internally.

Additionally, a RMD, Per, GTS, GFS-Cys109Ser, ColD, or ColC enzyme having above indicated degree of relatedness to the reference enzyme is only regarded as a variant, if it exhibits the relevant biological activity to a degree of at least 30% of the activity of the respective reference enzyme. The relevant "biological activity" in the context of the present invention is the "enzyme activity", i.e. the activity of the RMD, Per, GTS, GFS-Cys109Ser, ColD, or ColC enzyme variant to utilized the substrate GDP-6-deoxy-D-lyxo-4-hexylose and covert it into GDP-D-rhamnose, GDP-D-perosamine, GDP-deoxy-D-talose, GDP-6-deoxy-D-altrose, GDP-4-keto-3,6-dideoxy-D-mannose or GDP-L-colitose, respectively. The skilled person can readily assess whether a RMD, Per, GTS, GFS-Cys109Ser, ColD, or ColC enzyme variant has an enzyme activity of at least 30% of the enzyme activity of the respective reference RMD, Per, GTS, GFS-Cys109Ser, ColD, or ColC enzyme. Suitable assays, e.g. enzyme activity assays, for determining the "enzyme activity" enzyme variant compared to the enzyme activity of the respective reference enzyme are known to the person skilled in the art.

Preferably, the enzyme GDP-6-deoxy-D-lyxo-4-hexylose reductase (RMD) is from *Pseudomonas aeruginosa* (SEQ ID NO: 1). The enzyme GDP-6-deoxy-D-talose synthetase (GTS) is preferably from *Actinobacillus actinomycetemcomitans* (SEQ ID NO: 2). It is preferred that the enzyme GDP-perosamine synthetase (Per) is from *Vibrio cholerae* (SEQ ID NO: 3). Preferably, the GDP-4-keto-6-deoxymannose-3-dehydratase (ColD) is from *E. coli* (SEQ ID NO: 4). The use of GDP-L-colitose synthase (ColC) from *E. coli* is also preferred (SEQ ID NO: 7). The wild-type GDP-Fucose synthetase (GFS) is from *Cricetulus griseus* (Chinese hamster) (SEQ ID NO: 5). The GDP-Fucose synthetase Cys109Ser-(GFS-Cys109Ser) mutant from *Cricetulus griseus* (Chinese hamster) has the amino acid sequence of SEQ ID NO: 6.

As mentioned above, the invention encompasses variants of the enzymes using GDP-6-deoxy-D-lyxo-4-hexylose as a substrate. Thus, the present invention also covers variants of the above mentioned sequence identifier numbers, i.e. SEQ ID NO: 1 variants, SEQ ID NO: 2 variants, SEQ ID NO: 3 variants, SEQ ID NO: 4 variants, SEQ ID NO: 5 variants, SEQ ID NO: 6 variants, and SEQ ID NO: 7 variants. As to the structural and/or functional definition of said variants, it is referred to the aforementioned paragraphs.

The similarity of amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) *Proc. Natl. Acad. Sci. USA* 90: 5873-5877), with hmmalign (HMMER package, http//:hmmer.wustl.edu/) or with the CLUSTAL algorithm (Thompson, J. D., Higgins, D. G. & Gibson, T. J. (1994) *Nucleic acids Res.* 22, 4673-80) available e.g. on http://www.ebi.ac.uk/Tools/clustalw/ or on http://ebi.ac.uk/Tools/clustalw2/index.html or on http://npsa-pbil.ibcp.fr/cgi-bin/npsa_automat.pI?page=/NPSA/npsa_clustalw.html. Preferred parameters used are default parameters as they are set on http://www.ebi.ac.uk/Tools/clustalw/ or http://www.ebi.ac.uk/Tools/clustalw2/index.html. The grade of sequence identity (sequence matching) may be calculated using e.g. BLAST or BlastZ (or BlastX). A similar algorithm is incorporated into the BLASTP programs of Altschul et al. (1990) J. Mol. Biol. 215:403-410.

Preferably, the nucleic acid sequences of RMD, Per, GTS, ColD, ColC, or GFS-Cys109Ser are codon-optimized. The term "codon-optimized" as used in the context of the present invention means, for example, the removal of internal Tata boxes, chi sites, ribosome entry sites, RNA instability motifs, repeat sequences, intense RNA secondary structures and cryptic splice sites as well as the use of codons of higher utilization in eukaryotic (e.g. vertebrate) cells or of highly expressed genes in eukaryotic (e.g. vertebrate) cells.

The eukaryotic cell, e.g. vertebrate cell, further or alternatively to the enzyme comprises GDP-D-rhamnose, GDP-D-perosamine, GDP-deoxy-D-talose, GDP-6-deoxy-D-altrose, GDP-4-keto-3,6-dideoxy-D-mannose, and/or GDP-L-colitose to inhibit or prevent GDP-L-fucose synthesis as the inventors of the present invention have unexpectedly noticed that the supplementation, particularly the cytosolic supplementation, e.g. by intracytoplasmic injection, of the artificial sugars GDP-D-rhamnose, GDP-D-perosamine, GDP-deoxy-D-talose, GDP-6-deoxy-D-altrose, GDP-4-keto-3,6-dideoxy-D-mannose, and/or GDP-L-colitose positively contributes to the inhibition of fucose transfer in eukaryotic cells, e.g. vertebrate cells. The supplementation of the artificial sugar(s) GDP-6-deoxy-D-altrose, GDP-D-rhamnose, and/or GDP-D-perosamine is (are) particularly preferred.

It is preferred that the enzyme which uses GDP-6-deoxy-D-lyxo-4-hexylose as a substrate and which does not catalyze the reaction which converts GDP-6-deoxy-D-lyxo-4-hexylose into GDP-L-fucose is expressed from a nucleic acid sequence transiently present or stably maintained in the vertebrate cell, e.g. episomally or chromosomally.

The nucleic acid sequence encoding the enzyme, preferably GDP-6-deoxy-D-lyxo-4-hexulose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3- dehydratase (ColD), or GDP-L-colitose synthase (ColC) is integrated in an expression vector, which is used to transform the cell.

Suitable expression vectors comprise plasmids, cosmids, bacterial artificial chromosomes (BAC) and viral vectors. Preferably, non-viral expression vectors are used.

The expression of the nucleic acid encoding the enzyme is controlled by expression control sequences. The term "expression control sequences" refers to nucleotide sequences which are affect the expression in eukaryotic cells (e.g. vertebrate cells) of coding sequences to which they are operably linked. Expression control sequences are sequences which control the transcription, e.g. promoters, TATA-box, enhancers; post-transcriptional events, e.g. polyadenylation; and translation of nucleic acid sequences. Preferably, the nucleic acid sequence encoding the above enzymes is under control of a constitutive promoter, preferably under control of a human translocation elongation factor 2 (EF2) promoter. Other constitutive promoters are well known in the art.

It is preferred that the nucleic acid sequence encoding the enzyme RMD, Per, GTS, GFS-Cys109Ser, ColD or ColC in the expression vector is operably inked to eukaryotic, e.g. vertebrate, specific expression control sequences, which allow the expression of the nucleic acid sequence encoding the enzyme RMD, Per, GTS, GFS-Cys109Ser, ColD or ColC in the eukaryotic cell, e.g. vertebrate cell. As a result, the enzyme(s) RMD, Per, GTS, GFS-Cys109Ser, and/or ColD, ColD preferably in combination with ColC, are expressed in the eukaryotic cell, e.g. vertebrate cell, of the present invention in yields optimal for the desired effect. Depending on the nature of the enzyme and the cell used for expression these yields may be high moderate or low. It is easy for those skilled in the art to choose appropriate eukaryotic, e.g. vertebrate specific expression control sequences, to achieve high, moderate or low level of expression.

As a result, a molecule which would usually comprise (natural) fucose on its glycomoieties and/or amino acids in a eukaryotic cell, wherein the de novo pathway is not blocked, and which is produced in the eukaryotic cell of the present invention, e.g. in a eukaryotic cell comprising GTS and/or Per and a fucose analogue, lacks (natural) fucose on its glycomoieties and/or amino acids, but comprises instead of (natural) fucose a fucose analogue on its glycomoieties and/or amino acids.

As mentioned above, the efficient production of molecules comprising a fucose analogue strongly benefits from a deficient fucose de novo synthesis pathway. The blocking of the de novo pathway avoids competitive incorporation of natural fucose and drastically increases incorporation efficiency for the fucose analogue. Other preferred embodiments to disrupt/block the de novo pathway are described below.

GDP-mannose dehydratase (GMD) is an enzyme which usually catalyzes the reaction which converts GDP-mannose into GDP-6-deoxy-D-lyxo-4-hexylose and GDP-Fucose synthetase (GFS) is an enzyme which usually uses GDP-6-deoxy-D-lyxo-4-hexylose as a substrate and converts it into GDP-L-fucose (see FIG. 1, left hand panel). Thus, if no enzymatically active GMD and/or GFS is present in said cell, or if a GMD and/or GFS with a reduced enzymatic activity is present in said cell, the GDP-L-fucose synthesis pathway originating from GDP-D-mannose (de novo pathway) is blocked.

Thus, alternatively or additionally, it is preferred that the eukaryotic cell of the present invention (i) does not comprise an enzymatically active GDP-mannose dehydratase (GMD) or comprises a GDP-mannose dehydratase (GMD) having a reduced enzymatic activity, and/or (ii) does not comprise an enzymatically active GDP-Fucose synthetase (GFS) or comprises a GDP-Fucose synthetase (GFS) having a reduced enzymatic activity. With the term "reduced enzymatic activity" of GMD or GFS, a reduction/lowering of the biological activity of GMD or GFS is meant, i.e. the activity of GMD to utilize the substrate GDP-mannose and to convert it into GDP-6-deoxy-D-lyxo-4-hexylose or the activity of GFS to utilized the substrate GDP-6-deoxy-D-lyxo-4-hexylose and to covert it into GDP-L-fucose. Preferably the biological activity of GMD or GFS is reduced by 50% or 60%, more preferably by at least 70% or 80%, and most preferably by at least 90%, 95% or 99%, e.g. at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%. Said enzyme activity reduction may be achieved due to the introduction of mutations such one or more, e.g. 1, 2, 3, 4, 5, 6, 7, 8, 9, 10, 11, 12, 13, 14, or 15, addition(s), deletion(s), insertion(s) and/or substitution(s) into the amino acid sequence. The skilled person can readily assess whether the enzyme activity of GMD or GFS (e.g. GMD or GFS mutants), is reduced compared to fully (100%) active GMDs or GFSs (e.g. non-mutated wild-type GMDs or GFSs). Suitable enzyme activity assays are known to the person skilled in the art. However, as mentioned above, the reduction of the enzyme activity of GMD and/or GFS has to be to such a degree/level that the GDP-L-fucose synthesis pathway originating form GDP-D-mannose (de novo pathway) is blocked by at least 50%, preferably by at least 60% or 70%, more preferably by at least 80% or 90%, and most preferably by at least 95% or 100% (see above).

As a result, a molecule which would usually comprise (natural) fucose on its glycomoieties and/or amino acids in a eukaryotic cell, wherein the de novo pathway is not blocked, and which is produced in the eukaryotic cell of the present invention, e.g. in a eukaryotic cell comprising GMD or GFS and a fucose analogue, lacks (natural) fucose on its glycomoieties and/or amino acids, but comprises instead of (natural) fucose a fucose analogue on its glycomoieties and/or amino acids.

In preferred embodiments, said cell does not comprise an enzymatically active GDP-mannose dehydratase (GMD) as (i) the GMD is mutated so that it is not able to catalyze the reaction which converts GDP-mannose into GDP-6-deoxy-D-lyxo-4-hexylose, (ii) the gene encoding GMD is partially or fully knocked-out so that no enzymatically active GMD is expressed which is able to catalyze the reaction which converts GDP-mannose into GDP-6-deoxy-D-lyxo-4-hexylose, or (iii) the promoter region regulating the expression of the GMD gene is partially or fully deleted so that no enzymatically active GMD is expressed which is able to catalyze the reaction which converts GDP-mannose into GDP-6-deoxy-D-lyxo-4-hexylose, and/or said cell does not comprise an enzymatically active GDP-Fucose synthetase (GFS) as (i) the GFS is mutated so that it is not able to use GDP-6-deoxy-D-lyxo-4-hexylose as a substrate and to convert it into GDP-L-fucose, (ii) the gene encoding GFS is partially or fully knocked-out so that no enzymatically active GFS is expressed which is able to use GDP-6-deoxy-D-lyxo-4-hexylose as a substrate and to convert it into GDP-L-fucose, or (iii) the promoter region regulating the expression of the GFS gene is partially or fully deleted so that no enzymatically active GFS is expressed which is able to use GDP-6-deoxy-D-lyxo-4-hexylose as a substrate and to convert it into GDP-L-fucose.

It is also preferred to knock-down or to partially knock-down the enzymatic activity of GMD and/or GFS. The knock-down of the enzymatic activity of GMD and/or GFS may be achieved to the constitutive and stable expression of a specific siRNA or miRNA, e.g. episomally present in the cell, which blocks/inhibits the expression of GMD and/or GFS on the mRNA level.

The GMD and/or GFS mutants may be introduced into the eukaryotic cell of the present invention via protein microinjection, protein electroporation or protein lipofection. It is also possible to introduce the nucleic acid sequence encoding the GMD mutant and/or the nucleic acid sequence encoding the GFS mutant, preferably integrated in an expression vector, into the eukaryotic cell of the present invention via DNA microinjection, DNA electroporation, or DNA lipofection. In preferred embodiments, the GMD mutant and/or GFS mutant is expressed from a nucleic acid sequence transiently present or stable present in the eukaryotic cell of the present invention.

It is further preferred that the fucose salvage pathway is additionally blocked in the eukaryotic cell. Therefore, it is preferred to use growth media free of fucose and of fucosylated glycoproteins, when culturing the eukaryotic cells, e.g. vertebrate cells, of the present invention.

The growth medium or culture medium is instead spiked with a fucose analogue which is taken up by the eukaryotic cell, e.g. vertebrate cell, of the present invention (e.g. by active transport or passive diffusion), which is tolerated and metabolized by the eukaryotic cell, e.g. vertebrate cell, of the present invention via the salvage pathway, and which stable enough to be linked, instead of natural fucose, to the glycomoieties and/or amino acids in upstream cell culturing processes.

It is preferred that the eukaryotic cell, e.g. vertebrate cell, of the present invention further comprises at least one (acceptor) molecule which is/is capable of being a substrate for a fucosyltransferase (e.g. protein or lipid).

The term "(acceptor) molecule being/capable of being a substrate for a fucosyltransferase", as used in the context of the present invention, refers to any compound of interest, e.g. a protein, polypeptide, peptide, lipid, lipid fragment, or fusion protein, comprising glycomoieties and/or amino acids to which at least one fucose residue is attached, if produced in a cell having an unaltered fucosylation activity. Such a compound is a suitable substrate for a fucosyltransferase. A preferred (acceptor) molecule is accordingly a glycoprotein, glycopolypeptide, glycopeptide, glycolipid, glycolipid fragment, or glycosylated fusion protein. The term "(acceptor) molecule capable of being a substrate for a fucosyltransferase", as used in the context of the present invention, also refers to any compound of interest, e.g. a protein, polypeptide, peptide, lipid, lipid fragment, or fusion protein, so long as it is a prospective glycosylated compound, e.g. glycoprotein, glycopolypeptide, glycopeptide, glycolipid, glycolipid fragment, or glycosylated fusion protein to which at least one fucose residue can be attached, if produced in a cell having an unaltered fucosylation activity. Preferably the protein is not of prokaryotic origin. It is particularly preferred that the protein is a mammalian protein or derived therefrom.

The presence of a molecule capable of being a substrate for a fucosyltransferase in the eukaryotic cell, e.g. vertebrate cell, of the present invention, i.e. in a cell in which the de novo pathway is blocked and in which the salvage pathway is preferably additionally inhibited due to culturing in fucose deficient medium but which comprises a fucose analogue, leads to the production of a molecule which does not comprise (natural) fucose on its glycomoieties and/or amino acids but which comprises a fucose analogue on its glycomoieties and/or amino acids.

Thus, said molecule (e.g. protein or lipid) may be a molecule which (i) naturally comprises (natural) fucose on its glycomoieties and/or (ii) comprises a protein-O-fucosyltransferase recognition site in its structure (e.g. amino acid sequence).

Said protein-O-fucosyltransferase recognition site may be a naturally occurring recognition site such as a recognition site naturally present in the molecule structure (e.g. amino acid sequence), or may be a non-naturally occurring (artificial) recognition site such as a recognition site additionally introduced into the molecule structure (e.g. amino acid sequence) of said molecule (e.g. protein or lipid).

Preferably, said molecule (e.g. protein) comprises (e.g. naturally and/or artificially) one or more EGF-like repeats, e.g. 1, 2, 3, 4, 5, 6, 7, or 8, preferably 1 or 2, comprising a serine and/or threonine residue which is (are) recognized by a protein-O-fucosyltransferase, preferably by POFUT1. Said enzyme may add fucose sugars in O-linkage to serine or threonine residues between the second and third conserved cysteines in said EGF-like repeats. The protein is an inverting glycosyltransferase, which means that the enzyme uses GDP-L-fucose as a donor substrate and transfers the fucose in O-linkage to the protein producing fucose-α-O-serine/threonine. In the eukaryotic cell of the present invention, i.e. in a cell in which the de novo pathway is blocked and in which the salvage pathway is preferably additionally inhibited due to culturing in fucose deficient medium but which comprises a fucose analogue, said enzyme, i.e. the protein-O-fucosyltransferase, preferably POFUT1, attaches (preferentially or exclusively) a fucose analogue instead of (natural) fucose to its recognition sites.

More preferably, said EGF-like repeat is an EGF-like repeat with an amino acid sequence according to SEQ ID NO: 10 or a variant thereof which is at least 80% or 85%, more preferably 90% or 95%, most preferably 98% or 99%, e.g. 80, 81, 82, 83, 84, 85, 86, 87, 88, 89, 90, 91, 92, 93, 94, 95, 95, 96, 97, 98, or 99%, identical to said amino acid sequence. In preferred embodiments, the sequence identity is over a continuous stretch of at least 10, 12, 15, 17, 20, 22 or more amino acids, preferably over the whole length of the respective reference polypeptide (SEQ ID NO: 10). In particularly preferred embodiments, the sequence identity is at least 95% over the whole length, is at least 96% over the whole length, is at least 97% over the whole length, is at least 98% over the whole length, or is at least 99% over the whole length of the respective reference polypeptide (SEQ ID NO: 10). It is further particularly preferred that the above-mentioned variant is a functionally active variant. This means that the variations, e.g. in form of one or more, e.g. 1, 2, 3, 4, or 5, amino acid substitution(s), addition(s), insertion(s), and/or deletion(s), lie outside of the amino acid position(s) described above allowing the recognition of the protein-O-fucosylation site and/or the attachment of a fucose analogue to said site by a protein-O-fucosyltransferase. The person skilled in the art is aware of techniques how to assess whether a fucose analogue can still be attached to the EGF-like repeat variant comprised in the above mentioned molecules. One suitable technique is, for example, MALDI-TOF/TOF.

Most preferably, said EGF-like repeat (e.g. SEQ ID NO: 10 or a variant thereof) is attached to/comprised at the C-terminus and/or N-terminus of the molecule, e.g. protein.

It is, additionally or alternatively, further preferred that said molecule (e.g. protein) comprises (e.g. naturally and/or artificially) one or more thrombospondin repeats comprising a serine and/or threonine residue which is (are) recognized by a protein-O-fucosyltransferase, preferably by POFUT2. Said enzyme may add fucose sugars in 0 linkage to serine or threonine residues in Thrombospondin repeats. The protein is an inverting glycosyltransferase, which means that the enzyme uses GDP-L-fucose as a donor substrate and transfers the fucose in O linkage to the protein producing fucose-α-O-serine/threonine. In the eukaryotic cell of the present invention, i.e. in a cell in which the de novo pathway is blocked and in which the salvage pathway is preferably additionally inhibited due to culturing in fucose deficient medium but which comprises a fucose analogue, said enzyme, i.e. the protein-O-fucosyltransferase, preferably POFUT2, attaches (preferentially or exclusively) a fucose analogue instead of (natural) fucose to its recognition sites.

The term "a molecule which naturally comprises fucose on its glycomoieties", as used in the context of the present invention, refers to any compound which upon production in a eukaryotic cell, e.g. vertebrate cell, capable of adding fucose to glycomoieties, i.e. with an unaltered ability to add fucose to glycomoieties, comprises glycomoieties comprising at least one fucose residue. Such molecules comprise at least one or more sequence motifs recognized by a glycan transferring enzyme, e.g. comprising an Asp, Ser or Thr residue, preferably a tripeptide sequence Asn-X-Ser/Thr, wherein X is any amino acid except Pro. Preferred examples of cells (e.g. eukaryotic cells such as vertebrate cells) that produce molecules comprising glycomoieties with fucose are CHO, AGE1.HN, AGE1.CR, AGE1.CR.PIX, or AGE1.CS. Preferably such compounds are proteins fusion proteins or lipids. Preferably the proteins are of eukaryotic, preferably vertebrate most preferably of mammalian origin or derived therefrom. In the eukaryotic cell of the present invention, i.e. in a cell in which the de novo pathway is blocked and in which the salvage pathway is preferably additionally inhibited due to culturing in fucose deficient medium but which comprises a fucose analogue, said molecule comprises (preferentially or exclusively) a fucose analogue instead of (natural) fucose on its glycomoieties.

The molecule capable of being a substrate for a fucosyltransferase may also be a viral component. Said viral component can be any glycosylated entity such as that contained in an enveloped live virus, whether attenuated or wild type, an inactivated or split dead enveloped virus, an isolated or purified viral glycoprotein or a viral glycolipid, or a glycoprotein that is encoded and produced by a viral expression vector with which a producer cell is infected. To obtain a virus that has incorporated the fucose analogue on its viral components, the cell according to the present invention has to be used, i.e. a cell engineered for block in de novo synthesis of fucose and preferably also for abolished alpha-1,3-fucosyltransferase activity.

It is preferred that the molecule capable of being a substrate for a fucosyltransferase is a protein or polypeptide, preferably an endogenous or exogenous protein or polypeptide. The term "exogenous protein or polypeptide" means any protein or polypeptide that is either coming from the outside of the respective cell or that is expressed inside the cell from a nucleic acid introduced into the respective cell. The term "endogenous protein or polypeptide" refers to any protein that is encoded by the genome of the cell. Preferably, the protein or polypeptide of interest, namely the prospective glycoprotein or glycopolypeptide, is recombinantly expressed in the eukaryotic cell. It is preferred that said protein or polypeptide is expressed from a nucleic acid sequence transiently present or stably maintained in the eukaryotic cell. Suitable expression vectors and expression control sequences have been described above with respect to the enzyme. These can equally be used in the context of the expression of the nucleic acid encoding the protein of interest.

Thus, in a preferred embodiment of the present invention, the eukaryotic cell, e.g. vertebrate cell, comprises
(i) at least one polynucleotide comprising a nucleic acid sequence encoding the enzyme GDP-6-deoxy-D-lyxo-4-hexylose reductase (RMD), GDP-perosamine synthetase (Per), GDP-6-deoxy-D-talose synthetase (GTS), GDP-Fucose synthetase Cys109Ser-(GFS-Cys109Ser) mutant, GDP-4-keto-6-deoxymannose-3-dehydratase (ColD), or GDP-L-colitose synthase (ColC), operably linked to specific expression control sequences, which allow the expression of the nucleic acid sequence encoding the respective enzyme, and
(ii) at least one polynucleotide comprising a nucleic acid sequence encoding the protein of interest, namely the prospective glycoprotein, e.g. an antibody, such as IgG1, operably linked to specific expression control sequences, which lead to expression of the nucleic acid sequence encoding the protein of interest, e.g. an antibody, such as IgG1, in said cell.

As a result, (i) the enzyme(s) RMD, Per, GTS, GFS-Cys109Ser, and/or ColD, ColD preferably in combination with ColC, and (ii) the protein(s) of interest, namely the prospective glycoprotein(s), e.g. an antibody, such as IgG1, are expressed in the eukaryotic cell, e.g. vertebrate cell, of the present invention.

The polynucleotides mentioned above may be introduced via transfection, electroporation or lipofection into the cell. The transfection, electroporation or lipofection may be performed according to standard procedures known to the person skilled in the art. Following the introduction of foreign nucleic acids, transfected, electroporated or lipofected cells may be selected by applying selective pressure by adding, for example, antibiotics, e.g. G418, puromycin, neomycin or geneticin, to the culture medium. Suitable selection systems are well known in the art.

Preferably, the protein or polypeptide is an antigen binding protein or polypeptide, preferably an antibody, more preferably an IgG1 antibody, an antibody fragment, more preferably an antibody fragment comprising the Fc region of an antibody, an antibody fusion protein, more preferably an antibody fusion protein comprising the Fc region of an antibody, a virus protein, virus protein fragment, or an antigen. Another preferred protein is an enzyme, a cytokine, a lymphokine, an agonist, an antagonist, or a hormone.

Specific examples of desired proteins or polypeptides include, but are not limited to, insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL, G-CSF, GM-CSF, M-CSF, MCP-I and VEGF. Also included is the production of erythropoietin or any other hormone growth factor. Preferably, the afore-mentioned molecules have a therapeutic and/or diagnostic use.

The antibody may be a monoclonal antibody (including a full length antibody) or a polyclonal antibody. Preferably, the antibody or antibody fragment is selected from the group consisting of IgG (e.g. IgG1, IgG2, IgG3 and IgG4), IgA, IgE, IgM, and IgD, single chain antibodies, single domain antibodies, multispecific antibodies (e.g. bispecific antibodies), scFv, dsFv, scFab, a maxibody, nanobody, transbody, diabody, adnectin, evibody, DARpin, affibody, ankyrin, iMab, camelid-antibody, glycosylated single-domain antigen-binding fragments derived from a Camelid heavy chain-only antibody, an engineered lipocalin-type protein such as an anticalin, an affilin, or a Kunitz-domain, and knottin, followed by at least one, preferably two constant domains (Fc) of an immunoglobulin, preferably of human origin.

Preferably, the antibody or antibody fragment is
(i) a naturally occurring antibody or antibody fragment,
(ii) a non-naturally occurring antibody or antibody fragment, preferably an antibody mutant or antibody fragment mutant.

Said antibody mutant or antibody fragment mutant may also be designated as modified antibody or modified antibody fragment. Said naturally occurring antibody or naturally occurring antibody fragment may also be designated as non-modified antibody or non-modified antibody fragment.

In preferred embodiments, the (naturally occurring or modified) antibody comprises two heavy chains or the (naturally occurring or modified) antibody fragment comprises a heavy chain, more preferably the constant domain of a heavy chain (CH domain).

It is particularly preferred that the naturally occurring antibody comprises two heavy chains wherein each heavy chain has a naturally N-glycosylation site at asparagine N297 (numbered according to the Kabat numbering system), or that the naturally occurring antibody fragment comprises a heavy chain, more preferably the constant domain of a heavy chain (CH domain), having a naturally N-glycosylation site at asparagine N297 (numbered according to the Kabat numbering system).

It is further particularly preferred that the modified antibody comprises two heavy chains wherein each heavy chain has an artificial N-glycosylation site at asparagine N159, particularly generated due to the replacement of G161 by S161, and/or an artificial N-glycosylation site at asparagine N276, particularly generated due to the replacement of Y278 by S278 (all numbered according to the Kabat numbering system), or that the modified antibody fragment comprises a heavy chain, more preferably the constant domain of a heavy chain (CH domain), having an artificial N-glycosylation site at asparagine N159, particularly generated due to the replacement of G161 by S161, and/or an artificial N-glycosylation site at asparagine N276, particularly generated due to the replacement of Y278 by S278 (all numbered according to the Kabat numbering system).

Preferably, the above mentioned modified antibodies or modified antibody fragments differ from their respective wild-type/unmodified antibodies or antibody fragments in that they comprise, per heavy chain, more preferably per constant domain of a heavy chain (CH domain), one or more, e.g. 1, 2, 3, 4, 5, 6, 7, or 8, preferably 1, 2, 3, or 4, additional functional N-glycosylation sequons. This is particularly useful for the attachment of additional artificial N-glycans. Thus, said modified antibodies or modified antibody fragments can provide more than the two N-glycosylation sequons which may normally be present per antibody molecule (one per heavy chain or CH domain). This in turn allows the coupling of more than two fucose analogues per antibody molecule (one per heavy chain or CH domain) which can be attached to the additional artificial N-glycans.

The term "sequon", as used herein, refers to a sequence of three consecutive amino acids in a protein or polypeptide that can serve as the attachment site to a polysaccharide (sugar) called an N-linked-glycan. This is a polysaccharide linked to the protein or polypeptide via the nitrogen atom in the side chain of asparagine (Asn). A sequon is either Asn-X-Ser or Asn-X-Thr, where X is any amino acid except proline.

Thus, it is also particularly preferred that the modified antibody comprises two heavy chains wherein each heavy chain has a naturally N-glycosylation site at asparagine N297 and further an artificial N-glycosylation site at asparagine N159, particularly generated due to the replacement of G161 by S161, and/or an artificial N-glycosylation site at asparagine N276, particularly generated due to the replacement of Y278 by S278 (all numbered according to the Kabat numbering system), or that the modified antibody fragment comprises a heavy chain, more preferably the constant domain of a heavy chain (CH domain), having a naturally N-glycosylation site at asparagine N297 and further an artificial N-glycosylation site at asparagine N159, particularly generated due to the replacement of G161 by S161, and/or an artificial N-glycosylation site at asparagine N276, particularly generated due to the replacement of Y278 by S278 (all numbered according to the Kabat numbering system).

Accordingly, in a preferred embodiment, an antibody comprising two heavy chains or an antibody fragment comprising a heavy chain (H), preferably the constant domain of a heavy chain (CH domain), comprises one or more N-glycosylation sites selected from the group consisting of asparagine N297, asparagine N159 and asparagine N276 (all numbered according to the Kabat numbering system). In a particularly preferred embodiment, an antibody comprising two heavy chains comprises 1, 2, or 3 N-glycosylation sites selected from the group consisting of asparagine N297, asparagine N159 and asparagine N276 (all numbered according to the Kabat numbering system) per heavy chain, or an antibody fragment comprising a heavy chain (H), preferably the constant domain of a heavy chain (CH domain), comprises 1, 2, or 3 N-glycosylation sites selected from the group consisting of asparagine N297, asparagine N159 and asparagine N276 (all numbered according to the Kabat numbering system). As mentioned above, the N-glycosylation site at asparagine N159 is particularly generated due to the replacement of G161 by S161 and the N-glycosylation site at asparagine N276 is particularly generated due to the replacement of Y278 by S278 (all numbered according to the Kabat numbering system).

More preferably, the antibody or antibody fragment comprises an antibody heavy chain constant domain having an amino acid sequence according to SEQ ID NO: 8 or SEQ ID NO: 9, wherein the amino acids G161 (CH) and/or Y278 (CH) (numbered according to the Kabat numbering system) are substituted with serine. These substitutions allow the N-glycosylation at asparagine N159 and/or N276 (see above). Said antibody or antibody fragment may also comprise a functional naturally occurring N-glycosylation site at asparagine N297 (CH) (numbered according to the Kabat numbering system). Thus, such modified antibody may enable the defined attachment of between two to six fucose analogues, or such modified antibody fragment may enable the defined attachment of between one to three fucose analogues.

Also preferred are variants of the amino acid sequence according to SEQ ID NO: 8 (IgG1 CH Allele 01, human), wherein the amino acids G161 (CH) and/or Y278 (CH) (numbered according to the Kabat numbering system) are substituted with serine, which are at least 90%, more preferably at least 95%, most preferably at least 99%, e.g. 90, 91, 92, 93, 94, 95, 96, 97, 98, or 99%, identical to said amino acid sequence, or variants of the amino acid sequence according to SEQ ID NO: 9 (IgG1 CH Allele $O_2$, human), wherein the amino acids G161 (CH) and/or Y278 (CH) (numbered according to the Kabat numbering system) are substituted with serine, which are at least 90%, more preferably at least 95%, most preferably at least 99%, e.g. 90, 91, 92, 93, 94, 95, 96, 97, 98, or 99%, identical to said amino acid sequence. In preferred embodiments, the sequence identity is over a continuous stretch of at least 20, 25, 30, 35, 40, 50, 60, 70, 80, 90, 100, 120, or more amino acids, preferably over the whole length of the respective reference polypeptide. In particularly preferred embodiments, the sequence identity is at least 95% over the whole length, is at least 96% over the whole length, is at least 97% over the whole length, is at least 98% over the whole length, or is at least 99% over the whole length of the respective reference polypeptide.

It is further particularly preferred that the afore-mentioned variants are functionally active variants. This means that the variations, e.g. in form of one or more, e.g. 1, 2, 3, 4, 5, 6, 7, 8, 9, 10, 11, 12, 13, 14, or 15, amino acid substitution(s), addition(s), insertion(s), and/or deletion(s) in the above indicated ranges, lie outside of the amino acid position(s) or differ from the amino acid position(s) described above allowing the recognition of a N-glycosylation site and the attachment of additional artificial N-glycans and/or naturally occurring N-glycans to said site. This means that (i) a functionally active variant of the amino acid sequence according to SEQ ID NO: 8 or SEQ ID NO: 9, wherein G161 is replaced by S161 generating an N-glycosylation site at asparagine N159, has no amino acid variations at these positions by may vary in other amino acid positions within the above indicated ranges, (ii) a functionally active variant of the amino acid sequence according to SEQ ID NO: 8 or SEQ ID NO: 9, wherein Y278 is replaced by S278 generating an N-glycosylation site at asparagine N276 has no amino acid variations at these positions by may vary in other amino acid positions within the above indicated ranges, (iii) a functionally active variant of the amino acid sequence according to SEQ ID NO: 8 or SEQ ID NO: 9, wherein G161 is replaced by S161 generating an N-glycosylation site at asparagine N159 and Y278 is replaced by S278 generating an N-glycosylation site at asparagine N276 has no amino acid variations at these positions by may vary in other amino acid positions within the above indicated ranges. Said functional variants may further comprise an N-glycosylation site at asparagine N297 which is not mutated (all numbered according to the Kabat numbering system).

In other words, in the above-mentioned functionally active variants, the sequence motif(s) recognized by a glycan transferring enzyme, e.g. comprising an Asp, Ser or Thr residue, preferably a tripeptide sequence Asn-X-Ser/Thr, wherein X is any amino acid except Pro, is still present and not mutated.

The person skilled in the art is aware of techniques how to assess whether N-glycans can still be attached to the additional artificial N-glycans and/or naturally occurring N-glycans comprised in the above mentioned antibody or antibody fragment variants and, thus, whether a fucose analogue can still be coupled. One suitable technique is, for example, MALDI-TOF/TOF.

With respect to the Kabat numbering scheme it is referred to Kabat et al., 1983 E. A. Kabat, T. T. Wu, H. Bilofsky, M. Reid-Miller and H. Perry, Sequence of Proteins of Immunological Interest, National Institutes of Health, Bethesda (1983)). Although the boundaries of the Fc region may vary, the human IgG heavy chain Fc region is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al.

Preferably, the virus protein or virus protein fragment is comprised in the envelope membrane of an enveloped virus. It is particularly preferred that the virus protein is G or F protein from Respiratory Syncytial Virus and that the virus protein fragment is the extracellular fragment of said protein. A further aspect of the invention is a virus comprising said virus protein or virus protein fragment.

It is also preferred that the molecule capable of being a substrate for a fucosyltransferase is a lipid. Preferably, the lipid is a glyceroglycolipid, most preferably a galactolipid, a sulfolipid (SQDG), or a glycosphingolipids, most preferably a cerebroside (e.g. a galactocerebroside or a glucocerebroside), a ganglioside, a globoside, a sulfatide or a glycophosphosphingolipid.

The glycosphingolipid (GSL) is particularly preferred. Glycosphingolipids contain a hydrophobic ceramide anchor N-acylsphingosine and a hydrophilic head-group composed of saccharides. They are normally found at the outer surface of cell membranes. The composition of the saccharide-moiety is cell type specific and depends on the developmental stage of the organism or can change with the oncogenic state of a cell.

It is particularly preferred that the lipid is comprised in the envelope membrane of an enveloped virus.

A further aspect of the invention is a virus comprising said lipid. Another further aspect of the invention is a virus comprising said lipid and said protein. Most preferably, the virus protein and/or lipid are comprised in the envelope of an enveloped virus. As already mentioned above, the protein or lipid can be a virus protein or lipid which is comprised in the envelope membrane of an enveloped virus. Preferably, the enveloped virus is used entirely or in part as an active component of a viral vaccine. The term "viral vaccine" means a preparation of a weakened or killed virus that upon administration stimulates antibody production or cellular immunity against the virus but is incapable of causing severe infections.

The above mentioned virus can be introduced into the eukaryotic cell, e.g. vertebrate cell, via virus infection. The virus can also be introduced into the eukaryotic cell, e.g. vertebrate cell, by introducing nucleic acids encoding all or part of the virus to be produced. In the case it will be necessary to provide proteins required for replication, assembly etc., this is usually achieved by using viral producer cell lines capable of expressing one or more virus proteins. For example HEK293, Per.C6 and AGE1.HN cells express adenovirus E1A proteins and are, thus, capable of complementing DNA lacking E1 coding regions.

Fucosylation of molecules, e.g. proteins or lipids, comprising glycomoieties in eukaryotic cells (e.g. vertebrate cells) requires a nucleotide sugar, GDP-L-fucose, as a donor and also the presence of particular fucosyltransferases, which transfer the fucosyl residue from the donor to the acceptor molecule. In glycans from eukaryotic cells, e.g. vertebrate cells, fucose may be attached to the antennary GlcNAc via an alpha 1,3 linkage (terminal fucose) or to the asparagine-linked GlcNAc via an alpha 1,6 linkage (core fucose).

To achieve a homogenous, stable and site-directed attachment of the fucose analogue to the molecule such as protein, e.g. antibody, the attachment of a fucose analogue instead of a natural fucose via an alpha 1,6 linkage to the chitobiose core is preferred. Thus, the eukaryotic cell, e.g. vertebrate cell, of the present invention preferably comprises an enzymatically active alpha-1,6-fucosyltransferase. The (sole) presence of an enzymatically active alpha-1,6-fucosyltransferase is particularly preferred in the eukaryotic cell, e.g. vertebrate cell, of the present invention, if the production of fucose analogue coupled proteins is intended, which only comprise a 1,6 fucosylation site (e.g. natural, un-modified antibodies). This may further increase charge-homogeneity of the fucose analogue coupled to proteins via an alpha-1,6-fucosyltransferase N-glycosylation site.

Alternatively or additionally, the eukaryotic cell of the present invention preferably comprises an enzymatically active protein-O-fucosyltransferase. A protein-O-fucosyltransferase (POFUT1) is an enzyme usually responsible for adding fucose sugars in O-linkage to serine or threonine residues. The protein is an inverting glycosyltransferase, which means that the enzyme uses GDP-β-L-fucose as a donor substrate and transfers the fucose in O-linkage to the protein producing fucose-α-O-serine/threonine. In the eukaryotic cell of the present invention, it can attach fucose analogues instead of natural fucose in O-linkage to serine or threonine residues comprised in the molecule structure. The (sole) presence of a protein-O-fucosyltransferase is particularly preferred in the eukaryotic cell, e.g. vertebrate cell, of the present invention, if the production of fucose analogue coupled proteins is intended which comprise one or more, e.g. 1, 2, 3, or 4, EGF-like repeat(s) comprising a serine and/or threonine residue(s), wherein said residue(s) is (are) recognized by said enzyme. This may further increases charge-homogeneity of the fucose analogue coupled proteins via a protein-O-fucosylation site.

In another preferred embodiment, the eukaryotic cell of the present invention does not comprise an enzymatically active alpha-1,3-fucosyltransferase. Preferably, the alpha-1,3-fucosyltransferase enzyme activity is abolished due to the overexpression, more preferably due to the constitutive and/or stable overexpression, of a suppressor of alpha-1,3-fucosylation such as histone deacetylase 5 (Hdac5). It is also preferred that the cell does not comprise an enzymatically active alpha-1,3-fucosyltransferase as (i) said enzyme is mutated so that it is not functionally active anymore, (ii) the gene encoding said enzyme is partially or fully knocked-out so that no functionally active enzyme is expressed, or (iii) the promoter region regulating the expression of the gene of said enzyme is partially or fully deleted so that no functionally active enzyme is expressed. Knock-down of the alpha-1,3-fucosyltransferase using miRNAs and/or siRNAs may also be possible.

The absence of an enzymatically active alpha-1,3-fucosyltransferase is particularly preferred in the eukaryotic cell, e.g. vertebrate cell, of the present invention, if the production of fucose analogue coupled proteins (e.g. antibodies) is intended which comprise artificial introduced N-glycosylation sites beside naturally occurring N-glycosylation sites (e.g. the artificial introduced N-glycosylation site(s) at amino acid position N276 and/or N159 and the naturally occurring N-glycosylation site at amino acid position N297 (numbered according to the Kabat system) in antibodies). While said artificial N-glycosylation sites may be accessible (due to the specific glycan structure at this position) by an alpha-1,3-fucosyltransferase and alpha-1,6-fucosyltransferase, the naturally occurring N-glycosylation sites may be accessible (due to the specific glycan structure at this position) by an alpha-1,6-fucosyltransferase. Thus, to allow the generation of molecule-pharmaceutically active compound-conjugates with high coupling stability and homogeneity, the (sole) presence of an enzymatically active alpha-1,6-fucosyltransferase and the absence of an enzymatically active alpha-1,3-fucosyltransferase is preferred.

The use of a eukaryotic cell of the present invention which is preferably devoid of alpha-1,3-fucosyltransferase activity results in sole remaining protein-O-fucosyltransferase and alpha-1,6-fucosyltransferase activity and, thus, leaves the protein-O-linked amino acid site and the alpha-1,6-linked core fucosylation site as the only sites to which a fucose analogue may be attached. This allows the generation of fucose analogue coupled proteins with high coupling stability and homogeneity, particularly the generation of antibodies which comprise both N-glycosylation sites which can be recognized by a alpha-1,6-fucosyltransferase and amino acid residues which can be recognized by a protein-O-fucosyltransferase.

It is preferred that the eukaryotic cell is a vertebrate cell. It is particularly preferred that the vertebrate cell is a mammalian, a fish, an amphibian, a reptilian cell or an avian cell.

It is more preferred that
(i) the mammalian cell is a human, mouse, rat, hamster, canine or monkey cell, more particularly a Chinese hamster ovary (CHO) cell, a Syrian hamster fibroblast (BHK21) cell (ATCC CCL-10), a SP2/0-Ag14 cell (ATCC CRL-1581), a NS0 cell (ECACC No. 85110503), a human cervical carcinoma (HELA) cell (ATCC CCL 2), a human PER.C6 cell, or a human AGE1.HN cell,
(ii) the fish cell is a *Ictalurus punctatus* (channel catfish) cell, more particularly a *Ictalurus punctatus* (channel catfish) ovary (CCO) cell (ATCC CRL-2772),
(iii) the amphibian cell is a *Xenopus laevis* cell, more particularly a *Xenopus laevis* kidney cell (ATCC CCL-102),
(iv) the reptilian cell is an *Iguana iguana* cell, more particularly an *Iguana iguana* heart (IgH-2) cell (ATCC CCL-108), or
(v) the avian cell is an avian retina cell, more particularly a AGE1.CR.PIX cell, or an avian somite cell.

The cell line AGE1.CR.PIX was deposited with the DSMZ-Deutsche Sammlung von Mikroorganismen und Zellkulturen GmbH, Mascheroder Weg 1b, 38124 Braunschweig, Germany on Nov. 24, 2005 under accession number DSM ACC2749. The cell line AGE1.HN was deposited with the DSMZ-Deutsche Sammlung von Mikroorganismen und Zellkulturen GmbH, Mascheroder Weg 1b, 38124 Braunschweig, Germany on Nov. 4, 2005 under accession number DSM ACC2744.

As described above, it is particularly preferred that the cell is a Chinese hamster ovary (CHO) cell. CHO cells are cells which were originally isolated in 1952. Derivatives of parental lineage CHO pro-(specifically CHO-K1), which may be used herein, are CHO-S and CHO-SV cells. One variant of this lineage, DUKX B11, is modified to contain only one allele of the dhfr gene that is inactivated by mutation. Another CHO subline, DG44, diverges earlier from the common ancestor and lacks both alleles of dhfr (Urlaub et al., 1986, Proc Natl Acad Sci USA. 83 (2): 337-341). In most preferred embodiments of the present invention, the Chinese hamster ovary (CHO) cell is a CHO-K1 or CHO-DG44 cell.

CHO-K1 or CHO-DG44 cells are extensively applied in the production of recombinant proteins and antibodies. Despite the high flexibility of CHO cells in general, both CHO-K1 or CHO-DG44 cells have individual distinct features. CHO-K1 cells grow to higher peak cell densities, whereas DG44 cells usually show a higher specific productivity. Typically, media are not compatible between the two cell lineages. Preferred cell lines are summarized in the following Table 1:

TABLE 1

| CELL LINE | DEPOSITION NUMBER | ORIGIN |
| --- | --- | --- |
| NS0 | ECACC No. 85110503 | Mouse Myeloma |
| Sp2/0-Ag14 | ATCC CRL-1581 | Mouse Myeloma |
| BHK21 | ATCC CCL-10 | Baby Hamster Kindney |
| HELA | ATCC CCL 2 | Human cervical carcinoma |
| CHO | ECACC No. 8505302 | Chinese Hamster Ovary |
| CHO wild-type | ECACC 00102307 | Chinese Hamster Ovary |
| CHO-K1 | ATCC CCL-61 | Chinese Hamster Ovary |
| CHO-DUKX (= CHO duk$^-$, CHO/dhfr$^-$) | ATCC CRL-9096 | Chinese Hamster Ovary |
| CHO-DUKX B11 | ATCC CRL-9010 | Chinese Hamster Ovary |
| CHO-DG44 | not deposited at ATCC (Urlaub et al., 1983) | Chinese Hamster Ovary |
| CHO Pro-5 | ATCC CRL-1781 | Chinese Hamster Ovary |
| CHO-S | Invitrogen Cat No. 10743-029 | Chinese Hamster Ovary |

As mentioned above, the GDP-L-fucose synthesis pathway originating from GDP-D-mannose (de novo pathway) is blocked in the eukaryotic cell, e.g. vertebrate cell, of the present invention. In preferred embodiments of the present invention, the GDP-L-fucose analogue comprised in said cell does not exert an inhibitory activity on said pathway in addition to a negative feedback inhibition that would be exerted by GDP-L-fucose. Thus, in preferred embodiments of the present invention, said GDP-L-fucose analogue does not efficiently inhibit said synthesis pathway. In more preferred embodiments of the present invention, the GDP-L-fucose analogue does not inhibit said synthesis pathway. It is even more preferred that the de novo pathway is not inhibited by the GDP-L-fucose analogue itself or by any other fucose analogue which is additionally present in said cell. Particularly, neither the GDP-L-fucose analogue (intracellular metabolized form) nor any other GDP-L-fucose analogue precursor (e.g. L-fucose analogue) inhibits the GDP-L-fucose synthesis pathway originating from GDP-D-mannose (de novo pathway) as describe above.

It is also preferred that the fucose analogue (in any form) is not an inhibitor of a fucosyltransferase (e.g. a 1,6-fucosyltransferase, 1,3-fucosyltransferase, and/or O-linked fucosyltransferase, preferably 1,6-fucosyltransferase such as FUT8 protein). Such an inhibition is not desired as it may abolish or reduce the incorporation of the fucose analogue into nascent glycostructures of the above-described molecules and/or its attachment to amino acids comprised in the above-described molecule.

The term "fucose analogue", as used herein, is a compound which has a structure that allows, after incorporation of the L-fucose analogue into the glycomoieties of the molecule (e.g. protein, polypeptide, or lipid) mentioned above and/or after attachment of the L-fucose analogue to amino acids (amino acid recognition sites) comprised in the molecule (e.g. protein or polypeptide) mentioned above, the linkage of further pharmaceutically active compound to said molecule. The term "fucose analogue" preferably does not comprise any fucose molecule or fucose derivative that naturally occurs in eukaryotic cells.

It is preferred that the GDP-L-fucose analogue comprises one or more, e.g. 1, 2, 3, 4, 5, or 6, preferably 1 or 2, reactive and/or activated substitutions. Said one or more reactive and/or activated substitutions are suchlike that they allow, after incorporation of the L-fucose analogue into the glycomoieties of the molecule (e.g. protein, polypeptide, or lipid) mentioned above and/or after attachment of the L-fucose analogue to amino acids (amino acid recognition sites) comprised in the molecule (e.g. protein or polypeptide) mentioned above, the linkage of further pharmaceutically active compound to said molecule.

Preferably, fucose analogues including bioorthogonal fucose analogues or derivatives bear one or more functional group(s) for chemical coupling using different reactions including but not limited to ketoneaminooxy/hydrazide ligation (Mahal L K, Yarema K J, Bertozzi C R (1997) Science 276:1125-1128. Tai H C, Khidekel N, Ficarro S B, Peters E C, Hsieh-Wilson L C (2004) J Am Chem Soc 126:10500-10501.), Staudinger ligation (Saxon E, Bertozzi C R (2000) Science 287:2007-2010.), Michael addition (Sampathkumar S G, Li A V, Jones M B, Sun Z, Yarema K J (2006) Nat Chem Biol 2:149-152.), the Huisgen-Sharpless-Meldal Cu(I) catalyzed azide-alkyne cycloaddition (Click Chemistry, Huisgen, R. (1961). "Centenary Lecture-1,3-Dipolar Cycloadditions". Proceedings of the Chemical Society of London: 357; H. C. Kolb, M. G. Finn and K. B. Sharpless (2001). "Click Chemistry: Diverse Chemical Function from a Few Good Reactions". Angewandte Chemie International Edition 40 (11): 2004-2021, Tornoe, C. W.; Christensen, C.; Meldal, M. (2002). "Peptidotriazoles on Solid Phase: [1,2,3]-Triazoles by Regiospecific Copper(I)-Catalyzed 1,3-Dipolar Cycloadditions of Terminal Alkynes to Azides". Journal of Organic Chemistry 67 (9): 3057-3064. Axford J S (1999) Biochim Biophys Acta 1455:219-229., Dube D H, Bertozzi CR (2005) Nat Rev Drug Discov 4:477-488. U.S. Pat. No. 7,375,234, Copper-catalysed ligation of azides and acetylenes), palladium-catalyzed Suzuki Cross Coupling, between organobornic acid and aryl or vinyl halides, pseudo-halides (including triflates), alkyls, alkenyls and/or alkynyls (Baxter, et al., J. Am. Chem. Soc, 2003, 125, 7198-7199; Wu, et ai, J. Org. Chem., 2003, 68, 670-673 and Molander, et al., J. Org. Chem., 2002, 67, 8424-8429), palladium-catalyzed Hiyama coupling of C—C bond formation between aryl, alkenyl, or alkyl halides or pseudohalides and organosilanes (Lee et al, J. Am. Chem. Soc., 2003, 125, 5616-5617; Denmark, et al., J. Am. Chem. Soc, 1999, 121, 5821-5822; Li, et al., Synthesis, 2005, 3039-3044; Murata, et ai, Synthesis, 2001, 2231-2233; Lee, Org. Lett, 2000, 2053-2055)., palladium or nickel catalyzed Kumada cross coupling of Grignard reagents with alkyl, vinyl or aryl halides (Frisch, et ai, Angew. Chem., 2002, 114, 4218-4221). nickel or palladium catalyzed Negishi Coupling of organozinc compounds with various halides (aryl, vinyl, benzyl or allyl) (Hadei, et ai, Org. Lett., 2005, 7, 3805-3807; Huo, et ai, Org. Lett., 2003, 5, 423-425; Lutzen, et ai, Eur. J. Org. Chem., 2002, 2292-2297), palladium-catalyzed Heck reaction C—C coupling between aryl halides or vinyl halides and activated alkenes in the presence of a base (Chandrasekhar, et al., Org. Lett., 2002, 4, 4399-4401; Masllorens, et al., Org. Lett., 2003, 5, 1559-1561; Battistuzzi, et al., Org.

Lett, 2003, 5, 777-780; Mo, et al., J. Am. Chem. Soc, 2005, 127, 751-760; Hansen, et al., Org. Lett, 2005, 7, 5585-5587.), palladium-catalyzed Fukuyama Coupling of organozinc compounds with thioesters to form ketones (Tokuyama, et al., J. Braz. Chem. Soc, 1998, 9, 381-387), Sonogashira Coupling of terminal alkynes with aryl or vinyl halides using a palladium catalyst, a copper(I) cocatalyst, and an amine base (Liang, et al., J. Org. Chem., 2006, 71, 379-381; Gholap, et al., J. Org. Chem., 2005, 70, 4869-4872; Liang, et al., J. Org. Chem. 2005, 70, 391-393; Elangovan, et al., Org. Lett, 2003, 5, 1841-1844; Batey, et al., Org. Lett, 2002, 1411-1414)., copper(I) catalyzed Cadiot-Chodkiewicz coupling coupling of a terminal alkyne and an alkynl halide (Marino, et al., J. Org. Chem., 2002, 67, 6841-6844) and Eglinton, Glaser, or Hay reactions, (Gibtner, et al., Chem. Euro. J., 2002, 68, 408-432).

Preferably, the GDP-L-fucose analogue is synthesized from an L-fucose analogue. In preferred embodiments, the L-fucose analogue is added to the culture medium from which it is taken up by the eukaryotic cell of the present invention (e.g. by active transport or passive diffusion). The GDP-L-fucose analogue is then usually synthesized from an L-fucose analogue via the salvage pathway. It may also be possible to introduce a GDP-L-fucose analogue directly into the cell and, thus, to bypass the salvage pathway.

It is particularly preferred that the L-fucose analogue is a peracetylated fucose analogue, preferably a pyranosyl form of 1,2,3,4-tetraacetyl-azido-fucose, more preferably a pyranosyl form of 1,2,3,4-tetraacetyl-azido-6-fucose.

Other preferred fucose analogues are fucose analogues which comprise one or more, e.g. 1, 2, 3, 4, 5, or 6, preferably 1 or 2, of the chemical/functional group(s) indicated as chemical/functional group A or B in Table 2. Said chemical/functional groups allow chemical/functional coupling to the pharmaceutically active compound by any conjugation chemistry, e.g. by a conjugation chemistry as listed in Table 2.

TABLE 2

| Chemical Coupling Reaction | Functional Group A | Functional Group B | References |
| --- | --- | --- | --- |
| Ketoneaminooxy/ Hydrazide Ligation | Ketoneaminooxy-group | Hydrazide | Mahal LK, Yarema KJ, Bertozzi CR (1997) Science 276: 1125-1128. Tai HC, Khidekel N, Ficarro SB, Peters EC, Hsieh-Wilson LC (2004) J Am Chem Soc 126: 10500-10501. |
| Staudinger Ligation | Azide | Phosphine or phosphit | Saxon E, Bertozzi CR (2000) Science 287: 2007-2010. |
| Michael Addition | α,β-unsaturated Carbonyl, Nitril or Carbonic Acid Amide | Carbanion (deprotonated Carbonyl) | Sampathkumar SG, Li AV, Jones MB, Sun Z, Yarema KJ (2006) Nat Chem Biol 2: 149-152. |
| Huisgen-Sharpless-Meldal Cu(I) catalyzed azide-alkyne cycloaddition ("Click Chemistry") | Azide | Alkyne | Huisgen, R. (1961). "Centenary Lecture - 1,3-Dipolar Cycloadditions". Proceedings of the Chemical Society of London: 357. H. C. Kolb, M. G. Finn and K. B. Sharpless (2001). "Click Chemistry: Diverse Chemical Function from a Few Good Reactions". Angewandte Chemie International Edition 40 (11): 2004-2021. Tornoe, C. W.; Christensen, C.; Meldal, M. (2002). "Peptidotriazoles on Solid Phase: [1,2,3]-Triazoles by Regiospecific Copper(I)-Catalyzed 1,3-Dipolar Cycloadditions of Terminal Alkynes to Azides". Journal of Organic Chemistry 67 (9): 3057-3064. Axford JS (1999) Biochim Biophys Acta 1455: 219-229. Dube DH, Bertozzi CR (2005) Nat Rev Drug Discov 4: 477-488. U.S. Pat. No. 7,375,234, Copper-catalysed ligation of azides and acetylenes. |
| Suzuki Cross Coupling (palladium-catalyzed) | Organoboronic acid | Aryl or Vinyl Halides, Pseudo-Halides (including Triflates), Alkyls, Alkenyls and/or Alkynyls | Baxter, et al., J. Am. Chem. Soc, 2003, 125, 7198-7199. Wu, et ai, J. Org. Chem., 2003, 68, 670-673. Molander, et al., J. Org. Chem., 2002, 67, 8424-8429. |
| Hiyama Coupling (palladium-catalyzed) | aryl, alkenyl, or alkyl halides or pseudohalides | organosilanes | Lee et al., J. Am. Chem. Soc., 2003, 125, 5616-5617. Denmark, et al., J. Am. Chem. |

TABLE 2-continued

| Chemical Coupling Reaction | Functional Group A | Functional Group B | References |
|---|---|---|---|
| | | | Soc, 1999, 121, 5821-5822. Li, et al., Synthesis, 2005, 3039-3044. Murata, et al., Synthesis, 2001, 2231-2233. Lee, Org. Lett, 2000, 2053-2055. |
| Kumada Cross Coupling (palladium or nickel catalyzed) | Grignard reagents | Alkyl, Vinyl or Aryl halides | Frisch, et al., Angew. Chem., 2002, 114, 4218-4221. |
| Negishi Coupling (nickel or palladium catalyzed) | Organozinc compound | Aryl-, Vinyl-, Benzyl- or Allyl-Halides | Hadei, et al., Org. Lett, 2005, 7, 3805-3807. Huo, et al., Org. Lett., 2003, 5, 423-425. Lutzen, et al., Eur. J. Org. Chem., 2002, 2292-2297. |
| Heck reaction C-C coupling (palladium-catalyzed) | Aryl Halides or Vinyl Halides | Base activated Alkene | Chandrasekhar, et al., Org. Lett., 2002, 4, 4399-4401. Masllorens, et al., Org. Lett, 2003, 5, 1559-1561. Battistuzzi, et al., Org. Lett, 2003, 5, 777-780. Mo, et al., J. Am. Chem. Soc, 2005, 127, 751-760. Hansen, et al., Org. Lett, 2005, 7, 5585-5587. |
| Fukuyama Coupling (palladium-catalyzed) | Organozinc compound | Thioester | Tokuyama, et al., J. Braz. Chem. Soc, 1998, 9, 381-387. |
| Sonogashira Coupling (palladium catalyst, copper(1) cocatalyst, and an amine base) | terminal Alkyne | Aryl or Vinyl Halide | Liang, et al., J. Org. Chem., 2006, 71, 379-381. Gholap, et al., J. Org. Chem., 2005, 70, 4869-4872. Liang, et al., J. Org. Chem. 2005, 70, 391-393. Elangovan, et al., Org. Lett, 2003, 5, 1841-1844. Batey, et al., Org. Lett, 2002, 1411-1414. |
| Cadiot-Chodkiewicz coupling (copper(1) catalyzed) | terminal Alkyne | Alkynl halide | Marino, et al., J. Org. Chem., 2002, 67, 6841-6844. |
| Eglinton, Glaser, or Hay reactions | terminal Alkyne | terminal Alkyne | Gibtner, et al., Chem. Euro. J., 2002, 68, 408-432. |

It is preferred that only fucose analogues are selected for which the fucose kinase, the transporter and the fucosyltransferase are permissive.

The above mentioned chemical/functional groups may be attached at any C position in the fucose structure. However, a chemical/functional group attached at C-5 or C-6 is particularly preferred. The C-6 position is a methyl group in the native fucose molecule. In a preferred embodiment, the fucose analogue carries azido- or alkynyl-groups or metabolizable precursors of alkynyl- or azido-fucose analogues enabled for Huisgen Sharpless Meldal click chemistry.

In a second aspect, the present invention relates to a method for producing a molecule which comprises a fucose analogue comprising the steps of:
(i) providing a eukaryotic cell according to the first aspect, and
(ii) isolating the molecule comprising a fucose analogue from the cell in i).

Preferably, upon step i), the molecule which is capable of being a substrate for a fucosyltransferase, e.g. a protein or polypeptide, is expressed in the cell in i).

It is also preferred that the cell is cultured prior to the isolation of the molecule in step (ii). Culturing may be performed according to standard procedures readily available to the skilled person. It is particularly preferred that the eukaryotic cell is cultured prior to the isolation of the molecule in step (ii) in a cell culture medium devoid of natural fucose or a metabolizable precursor of natural fucose. Instead of natural fucose or a metabolizable precursor of natural fucose, an effective amount of a fucose analogue is added to the culture medium. In this context, the term "effective amount" refers to an amount of the analogue which is sufficient so that the fucose analogue is incorporated into nascent glycostructures and/or added to amino acids. The amount of the fucose analogue that is effective can be determined by standard cell culture methodologies (see examples). For example, cell culture assays may be employed to help to identify optimal dosage ranges. The precise amount to be employed also depends on the time of administration, the cell type used, the cell density and the like. Effective doses may be extrapolated from dose-response curves derived form in vitro model test systems. In addition, the skilled person is able to analyse the molecule structure of the molecule produced with the method of the second aspect of the present invention in order to determine the presence of fucose analogues attached to or incorporated into said molecule structure. As an example, MALDI-TOF/TOF could be used (see also the methods indicated above). Other methods to determine the molecule structure, particularly the sugar structure, include hydazinolysis or enzyme digestion. In some embodiments, the fucose analogue is present in the culture medium at a concentration of between 0.1 nM to 50 mM or of between 10 nM to 50 mM, preferably of between 10 nM to 10 mM, more preferably of between 100 nM to 5 mM, 100 nM to 3 mM, or 100 nM to 2 mM, e.g. 10 nM, 20 nM, 30 nM, 40 nM, 50 nM, 60 nM, 70 nM, 80 nM, 90 nM, 100 nM, 110 nM, 120 nM, 130 nM, 140 nM, 150 nM, 160 nM, 170 nM, 180 nM, 190 nM, 200 nM, 250 nM, 300 nM, 350 nM, 400 nM, 450 nM, 500 nM, 600 nM, 700 nM, 800 nM, 900 nM, 1 mM, 1.5 mM, 2 mM, 2.5 mM, 3 mM, 3.5 mM, 4 mM, 4.5 mM, 5 mM, 10 mM, 20 mM, 30 mM, 40 mM, or 50 mM.

The molecule, e.g. protein, polypeptide, or lipid, comprising a fucose analogue on its glycomoieties and/or amino acids can be readily isolated in step ii) from the eukaryotic cell, e.g. vertebrate cell. Various isolation procedures are known in the art for molecules enclosed inside eukaryotic cells (e.g. vertebrate cells) or secreted from such cells comprising the modified molecules. Such methods typically involve cell harvest, disintegration and fractionation/purification in the case of intracellular molecules and generation of a cell free culture supernatant followed by purification of secreted molecules.

An extraction procedure that is useful according to the invention does not interfere with modified molecules to be isolated. For example, extraction is preferably performed in the absence of strong detergents and reducing agents, or any agent that may induce protein denaturation.

It will be understood by a skilled person that the molecule, e.g. protein, polypeptide, or lipid, which comprises a fucose analogue, e.g. on its glycomoieties and/or amino acids, produced in the method of the second aspect of the present invention is a glycomolecule, e.g. a glycoprotein, glycopolypeptide, or glycolipid.

In a third aspect, the present invention relates to a molecule comprising a fucose analogue obtainable by the method of the second aspect. Said molecule is a molecule as set out above with respect to the first aspect and said fucose analogue is a fucose analogue as set out above with respect to the first aspect. Preferably, said fucose analogue comprises one or more, e.g. 1, 2, 3, 4, 5, or 6, preferably 1, or 2, reactive or activated substitutions for binding a pharmaceutically active compound. Preferred fucose analogues are fucose analogues which comprise one or more, e.g. 1, 2, 3, 4, 5, or 6, preferably 1 or 2, of the chemical/functional group(s) indicated as chemical/functional group A or B in Table 2. Said chemical/functional groups allow chemical/functional coupling/binding to the pharmaceutically active compound by any conjugation chemistry, e.g. by a conjugation chemistry as listed in Table 2 (see also first aspect). It is particularly preferred that the protein or polypeptide is an antigen binding protein or polypeptide, preferably an antibody, an antibody fragment, a virus protein, a virus protein fragment, a hormone, or an antigen. It is also particularly preferred that the lipid is a glyceroglycolipid, most preferably a galactolipid, a sulfolipid (SQDG), or a glycosphingolipids, most preferably a cerebroside (e.g. a galactocerebroside or a glucocerebroside), a ganglioside, a globoside, a sulfatide or a glycophosphosphingolipid. Preferably, the lipid, e.g. ganglioside, is comprised in the membrane of an enveloped virus. Most preferably, the virus protein and/or lipid are comprised in the envelope of an enveloped virus (see also first aspect).

In a further aspect, the present invention provides a composition of molecules according to the third aspect. In said composition, the molecules according to the third aspect comprise preferably to 50%, more preferably to 60% or 70%, even more preferably to 80% or 90%, and most preferably to 95% or 100%, e.g. to 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, or 100%, a fucose analogue attached to its glycomoieties and/or amino acids. It is particularly preferred that the molecules according to the third aspect comprise an identical number of fucose analogues attached to its glycomoieties and/or amino acids, e.g. 1, 2, 3, 4, 5, 6, 7, or 8 fucose analogues.

In a fourth aspect, the present invention relates to a method for producing a conjugate comprising a molecule which comprises a fucose analogue and a pharmaceutically active compound comprising the steps of:
(i) carrying out the method of the second aspect, and
(ii) covalently coupling a pharmaceutically active compound via the fucose analogue to the molecule comprising said fucose analogue.

Said molecule is a molecule as set out above with respect to the first aspect and said fucose analogue is a fucose analogue as set out above with respect to the first aspect.

The term "pharmaceutically active compound", as used herein, refers to any compound being pharmaceutically useful or having a pharmaceutical effect. Preferably, said compound contains one or more, e.g. 1, 2, 3, 5, or 6, preferably 1 or 2, chemical/functional group(s), e.g. one or more of the chemical/functional group(s) indicated as chemical/functional group A or B in Table 2, that allow(s) chemical/functional coupling to the fucose analogue by any conjugation chemistry, e.g. by a conjugation chemistries as listed in Table 2. It should be noted that if a chemical/functional group as indicated as chemical/functional group A has been chosen for the pharmaceutically active compound, the respective chemical/functional group as indicated as chemical/functional group B has to be chosen for the fucose analogue in order to allow efficient and successful coupling of a pharmaceutically active compound via the fucose analogue to the molecule comprising said fucose analogue. In turn, if a chemical/functional group as indicated as chemical/functional group B has been chosen for the pharmaceutically active compound, the respective chemical/functional group as indicated as chemical/functional group A has to be chosen for the fucose analogue in order to allow efficient and successful coupling of a pharmaceutically active compound via the fucose analogue to the molecule comprising said fucose analogue.

Preferably, the pharmaceutically active compound contains an alkynyl- or azido-group that allows functional coupling to the alkynyl- or azido-modified fucose analogue incorporated into the protein-linked glycostructure or attached to the amino acid sequence. The pharmaceutically active compound may be a cytotoxic drug intended for therapy against tumors or chronic infectious diseases, including but not limited to compounds which are 100 to 1000 fold more toxic than the classical chemotherapeutic drugs. Such compounds include but are not limited to the extremely toxic calicheamicin and caliceamicin derivatives, auristatin or auristatin derivatives, maytansin, maytansin derivatives or maytansinoids such as DM1 and the very toxic DNA intercalating anthracycline antibiotics, doxorubicin, daunorubicin, epirubicin, esorubicin and idarubicin. Moreover, the pharmaceutically active compounds may include but are not limited to vinca alkaloids such as vincristin, vinblastin, vindesin, vinorelbin, taxanes such as paclitaxel, docetaxel, toxalbumins such as ricin, abrin, modeccin, viscumin, volkensin, topoisomerase inhibitors such as etoposid, teniposid, irinotecan, topotecan, actinomycines such as actinomycin D, dactinomycin, mitoxanthrone, amsacrin, and other extremely poisonous compounds such as phalloidin, alpha-amanitin, alflatoxin, dolastatin, methothrexate, miltefosin, imatinib and enzymatically active asparaginases and RNAses such as Barnase, Onconase, angiogenin ribonuclease, human pancreatic RNase, bovine seminal RNase, and eosinophil derived neurotoxin (EDN). The pharmaceutically active compound can also be a pharmacokinetic half life extender including but not limited to artificial synthetic polysialylated oligosaccharides, polyethylenglycol (PEG), homo-amino acid polymer (HAP), hydroxyethylstarch (HES) and albumin. The pharmaceutically active compound can also be an adjuvant including but not limited to β-glucans, squalenes, block copolymer (titer-max), cytokines, diterpene alcohols, preferably a phytol, bacterial monophosphoryl lipid A, trehalose dicorynomycolate, rhamnose and rhamnose containing oligosaccharides, saponines, Toll-like receptor agonists such as LPS, lipoproteins, lipopeptides, flagellin, double-stranded RNA, unmethylated CpG islands, U-rich single strand RNA, imiquimod, haemaglutinin. From the above mentioned toxins, fragments could be used. Toxins or toxin fragments as pharmaceutically active compounds are particularly preferred.

In a fifth aspect, the present invention relates to a conjugate comprising a molecule which comprises a fucose analogue and a pharmaceutically active compound obtainable by the method of the fourth aspect.

In a further aspect, the present invention provides a composition of conjugates comprising a molecule which comprises a fucose analogue and a pharmaceutically active compound according to the fifth aspect. In said composition, the conjugates according to the fifth aspect comprise preferably to 50%, more preferably to 60% or 70%, even more preferably to 80% or 90%, and most preferably to 95% or 100%, e.g. to 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99%, or 100%, a fucose analogue attached to its glycomoieties and/or amino acids and a pharmaceutically active compound attached to said fucose analogue. It is particularly preferred that the conjugates according to the fifth aspect comprise an identical number of fucose analogues attached to its glycomoieties and/or amino acids, e.g. 1, 2, 3, 4, 5, 6, 7, or 8 fucose analogues, to which a pharmaceutically active compound is conjugated.

In a sixth aspect, the present invention relates to a conjugate which comprises a protein or polypeptide comprising one or more of the following structures:

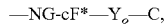

—NG-cF*—Y$_o$—C, wherein each is attached to an N-glycosylation site comprised in said protein or polypeptide,
NG is an N-linked glycomoiety of said protein or polypeptide,
cF* is a core fucose analogue,
Y is a spacer unit, wherein o is an integer of 0 or 1, and
C is a pharmaceutically active compound.

The spacer unit Y may be absent (o=0) or present (o=1). Suitable spacer units such amino acid linker are known to the person skilled in the art. It will be clear for the person skilled in the art that the expression "-" in the conjugates described herein refers to a "covalent bond.

The protein or polypeptide is preferably a protein or polypeptide as described with respect to the first aspect of the present invention, the fucose analogue is preferably a fucose analogue as described with respect to the first aspect of the present invention and/or the pharmaceutically active compound is preferably a pharmaceutically active compound as described with respect to the fourth aspect of the present invention. Further, the protein comprising a fucose analogue may be a protein according to the third aspect of the present invention, or the conjugate may be a conjugate comprising a molecule comprising a fucose analogue and a pharmaceutically active compound according to the fifth aspect of the present invention.

In a preferred embodiment, the conjugate comprises a protein or polypeptide comprising between 1 to 8, preferably 1 to 6, more preferably 1 to 3, e.g. 1, 2, 3, 4, 5, 6, 7, or 8, of the following structures: —NG-cF*—Y$_o$—C, wherein each is attached to an N-glycosylation site comprised in said protein or polypeptide.

Preferably, the glycomoiety is an N-linked glycomoiety of the complex type, more preferably the N-linked glycomoiety of the complex type has the glycostructure G0F*, G0F*-GlcNAc, G1F* or G2F* (see above structure definitions).

It is preferred that the polypeptide which is comprised in the conjugate is an antibody fragment, e.g. an antibody fragment as described with respect to the first aspect of the present invention. It is particularly preferred that the polypeptide which is comprised in the conjugate is an antibody heavy chain (H), preferably the constant domain of a heavy chain (CH domain).

It is more preferred that the conjugate comprises an antibody heavy chain (H), preferably the constant domain of a heavy chain (CH domain), comprising one or more, e.g. 1, 2, or 3, of the following structures: —NG-cF*—Y$_o$—C, wherein each is attached to an N-glycosylation site selected from the group consisting of asparagine N297, asparagine N159, and asparagine N276 (numbered according to the Kabat numbering system) comprised in said antibody heavy chain (H), preferably constant domain of said heavy chain (CH domain).

Thus, in a most preferred embodiment,
(i) one —NG-cF*—Y$_o$—C structure is attached to the N-glycosylation site at asparagine N297, asparagine N159, or asparagine N276 comprised in said antibody heavy chain, preferably constant domain of said heavy chain, or
(ii) one —NG-cF*—Y$_o$—C structure is attached to the N-glycosylation site at asparagine N297, one —NG-cF*—Y$_o$—C structure is attached to the N-glycosylation site at asparagine N159, and/or one —NG-cF*—Y$_o$—C structure is attached to the N-glycosylation site at asparagine N276 (all numbered according to the Kabat numbering system) comprised in said antibody heavy chain, preferably constant domain of said heavy chain.

The N-glycosylation site at asparagine N159 is particularly generated due to the replacement of G161 by S161 and the N-glycosylation site at asparagine N276 is particularly generated due to the replacement of Y278 by S278 (all numbered according to the Kabat numbering system). Thus, the above-mentioned antibody heavy chain (H), particularly the constant domain of a heavy chain (CH domain), comprised in the conjugate, preferably further comprises the point mutations G161→S161 (G161 replaced by S161) and/or Y278→S278 (Y278 replaced by S278) (all numbered according to the Kabat numbering system).

More preferably, the antibody heavy chain constant domain has an amino acid sequence according to SEQ ID NO: 8 or SEQ ID NO: 9, wherein the amino acids G161 (CH) and/or Y278 (CH) (numbered according to the Kabat numbering system) are substituted with serine. Also preferred are variants, particularly functionally active variants, of said sequences. As to the further characterization of said variants, it is referred to the first aspect of the present invention.

In the more and most preferred embodiments mentioned above, the fucose analogue is preferably a peracetylated fucose analogue, preferably a pyranosyl form of 1,2,3,4-tetraacetyl-azido-fucose, more preferably a pyranosyl form of 1,2,3,4-tetraacetyl-azido-6-fucose, and the pharmaceutically active compound is preferably a toxin or a toxin fragment.

In a preferred embodiment, the conjugate comprises 1, 2, or 3 cF*-linked pharmaceutically active compounds.

Preferably, the protein or polypeptide, e.g. antibody fragment such as an antibody heavy chain (H), preferably the constant domain of a heavy chain (CH domain), comprised in the above-mentioned conjugate further comprises one or more, e.g. 1, 2, 3, or 4, preferably 1 or 2, EGF-like repeats comprising a serine and/or threonine residue to which the following structure:

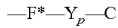

is attached, wherein
F* is a fucose analogue moiety directly linked to said serine and/or threonine residue,
Y is a spacer unit, wherein p is an integer of 0 or 1, and
C is a pharmaceutically active compound.

The spacer unit Y may be absent (p=0) or present (p=1). Suitable spacer units such amino acid linker are known to the person skilled in the art. As to the preferred fucose analogues, it is referred to the first aspect of the present invention and as to the preferred pharmaceutically active compounds it is referred to the fourth aspect of the present invention. As specified in the more and most preferred embodiments mentioned above, the fucose analogue is preferably a peracetylated fucose analogue, preferably a pyranosyl form of 1,2,3,4-tetraacetyl-azido-fucose, more preferably a pyranosyl form of 1,2,3,4-tetraacetyl-azido-6-fucose, and the pharmaceutically active compound is preferably a toxin or a toxin fragment.

As to the definition/description of the EGF-like repeat, it is also referred to the first aspect of the present invention. Said EGF-like repeats may be located within the amino acid sequence of said protein or polypeptide or may be comprised at the N-terminus and/or C-terminus of said protein or polypeptide. Preferably, said EGF-like repeat is comprised at the C-terminus and/or N-terminus of the protein or polypeptide, e.g. antibody fragment such as an antibody heavy chain (H), preferably the constant domain of a heavy chain (CH domain). More preferably, said EGF-like repeat is an EGF-like repeat with an amino acid sequence according to SEQ ID NO: 10 or a variant thereof which is at least 80% or 85%, more preferably 90% or 95%, most preferably 98% or 99%, e.g. 80, 81, 82, 83, 84, 85, 86, 87, 88, 89, 90, 91, 92, 93, 94, 95, 95, 96, 97, 98, or 99%, identical to said amino acid sequence. As to the further characterization of a variant of SEQ ID NO: 10, it is also referred to the first aspect of the present invention.

In a preferred embodiment, the conjugate comprises 1, 2, or 3 cF*-linked pharmaceutically active compounds and 1 or 2 F*-linked pharmaceutically active compounds.

The antibody heavy chain (CH), preferably the constant domain of a heavy chain (CH domain may also be comprised in a polypeptide to which the EGF-like repeat (e.g. SEQ ID NO: 10) is N-terminally and/or C-terminally added.

In a further aspect, the present invention relates to an antibody comprising two conjugates as defined in the sixth aspect. Said conjugates may comprise an antibody heavy chain (H), preferably the constant domain of a heavy chain (CH domain), as defined above.

In a preferred embodiment, the antibody comprises two conjugates each comprising 1, 2, 3, or 4 cF*-linked pharmaceutically active compounds and preferably 1 or 2 F*-linked pharmaceutically active compounds.

In a seventh aspect, the present invention relates to a conjugate which comprises a protein or polypeptide comprising one or more, e.g. 1, 2, 3, or 4, preferably 1 or 2, EGF-like repeats comprising a serine and/or threonine residue to which the following structure:

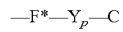

is attached, wherein
F* is a fucose analogue moiety directly linked to said serine and/or threonine residue,
Y is a spacer unit, wherein p is an integer of 0 or 1, and
C is a pharmaceutically active compound.

The spacer unit Y may be absent (p=0) or present (p=1). Suitable spacer units such amino acid linker are known to the person skilled in the art.

The protein or polypeptide is preferably a protein or polypeptide as described with respect to the first aspect of the present invention, the fucose analogue is preferably a fucose analogue as described with respect to the first aspect of the present invention and/or the pharmaceutically active compound is preferably a pharmaceutically active compound as described with respect to the fourth aspect of the present invention. Further, the protein comprising a fucose analogue may be a protein according to the third aspect of the present invention, or the conjugate may be a conjugate comprising a molecule comprising a fucose analogue and a pharmaceutically active compound according to the fifth aspect of the present invention.

It is preferred that the polypeptide which is comprised in the conjugate is an antibody fragment, e.g. an antibody fragment as described with respect to the first aspect of the present invention. It is particularly preferred that the polypeptide which is comprised in the conjugate is an antibody heavy chain (H), preferably the constant domain of a heavy chain (CH domain).

It is further preferred that the fucose analogue is a peracetylated fucose analogue, preferably a pyranosyl form of 1,2,3,4-tetraacetyl-azido-fucose, more preferably a pyranosyl form of 1,2,3,4-tetraacetyl-azido-6-fucose, and that the pharmaceutically active compound is a toxin or a toxin fragment.

As to the definition/description of the EGF-like repeat, it is also referred to the first aspect of the present invention. Said EGF-like repeats may be located within the amino acid sequence of said protein or polypeptide or may be comprised at the N-terminus and/or C-terminus of said protein or polypeptide. Preferably, said EGF-like repeat is comprised at the C-terminus and/or N-terminus of the protein or polypeptide, e.g. antibody fragment such as an antibody heavy chain (H), preferably the constant domain of a heavy chain (CH domain). More preferably, said EGF-like repeat is an EGF-like repeat with an amino acid sequence according to SEQ ID NO: 10 or a variant thereof which is at least 80% or 85%, more preferably 90% or 95%, most preferably 98% or 99%, e.g. 80, 81, 82, 83, 84, 85, 86, 87, 88, 89, 90, 91, 92, 93, 94, 95, 95, 96, 97, 98, or 99%, identical to said amino acid sequence. As to the further characterization of a variant of SEQ ID NO: 10, it is also referred to the first aspect of the present invention.

In a preferred embodiment, the conjugate comprises 1, 2, 3, or 4, preferably 1 or 2, F*-linked pharmaceutically active compounds.

The antibody heavy chain (CH), preferably the constant domain of a heavy chain (CH domain may also be comprised in a polypeptide to which the EGF-like repeat (e.g. SEQ ID NO: 10) is N-terminally and/or C-terminally added.

In a further aspect, the present invention relates to an antibody comprising two conjugates as defined in the seventh aspect. Said conjugates may comprise an antibody heavy chain (H), preferably the constant domain of a heavy chain (CH domain), as defined above.

In a preferred embodiment, the antibody comprises two conjugates each comprising 1, 2, 3, or 4, preferably 1 or 2, F*-linked pharmaceutically active compounds.

In the above-mentioned conjugates, the pharmaceutically active compound is linked to the protein backbone at a given site by a homogenous glycostructure or sub-glycostructure—a homogenous glycostructure being an O-linked fucose residue directly linked to an amino acid side chain of the protein backbone, a homogenous sub-glycostructure being the two proximal sugar-residues of the N-linked chitobiose core of a complex N-glycan, i.e. the asparagine-linked N-acetylglucosamine and its alpha-1,6-linked core-fucose residue. Compared to undefined protein—conjugates where the functional compound is coupled via other terminal sugars of a microheterogeneous glycostructure, such defined and homogenous fucose-linked conjugates as described herein offer the practical benefit of enhanced lot consistency, easier analytics for product comparability and coupling efficiency and a more predictable stability profile.

In an eighth aspect, the present invention relates to a pharmaceutical composition comprising
(i) the conjugate according to the sixth aspect or a pharmaceutically acceptable salt thereof, or
(ii) the antibody comprising two conjugates according to the sixth aspect or a pharmaceutical acceptable salt thereof.

In a ninth aspect, the present invention relates to a pharmaceutical composition comprising
(i) the conjugate according to the seventh aspect or a pharmaceutically acceptable salt thereof, or
(ii) the antibody comprising two conjugates according to the seventh aspect or a pharmaceutically acceptable salt thereof.

The term "pharmaceutically acceptable salt" refers to a salt of a compound identifiable by the methods of the present invention or a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci. 66:1-19 (1977)).

Preferably, the pharmaceutical composition further comprises one or more pharmaceutically acceptable excipient(s) and/or carrier(s).

The term "pharmaceutically acceptable excipient" when used herein is intended to indicate all substances in a pharmaceutical formulation which are not active ingredients such as, e.g., carriers, binders, lubricants, thickeners, surface active agents, preservatives, emulsifiers, buffers, flavoring agents, or colorants.

The term "pharmaceutically acceptable carrier" includes, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

The pharmaceutical compositions of the present invention may be formulated in various ways well known to one of skill in the art and as described above.

The pharmaceutical compositions are preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In a tenth aspect, the present invention relates to
(i) a conjugate according to the sixth aspect, an antibody comprising two conjugates according to the sixth aspect, or a pharmaceutical composition according to the eight aspect, or
(ii) a conjugate according to the seventh aspect, an antibody comprising two conjugates according to the seventh aspect, or a pharmaceutical composition according to the ninth aspect for treating, ameliorating, or preventing cancer or diseases caused by infections.

The treatment of cancer may involve the killing or inhibiting the proliferation of cancer/tumor cells and/or the infections may be viral or bacterial infections. Therefore, it is particularly preferred that the pharmaceutically active compound comprised in said conjugates is a toxin or a toxin fragment (see above). Such treatment, for example, involves the administration of an amount of the conjugate or antibody effective to kill or inhibit the proliferation of the tumor cells, cancer cells, immune cells or infected cells. The dosages, however, may be varied depending upon the requirements of the patient, the severity of the condition being treated, and the compound being employed. For treating, ameliorating, or preventing said conditions, the conjugates, antibodies or pharmaceutical compositions of the present invention can be administered to an animal patient, preferably a mammalian patient, preferably a human patient, orally, buccally, sublingually, intranasally, via pulmonary routes such as by inhalation, via rectal routes, or parenterally, for example, intracavernosally, intravenously, intra-arterially, intraperitoneally, intrathecally, intraventricularly, intraurethrally intrasternally, intracranially, intramuscularly, or subcutaneously.

In an eleventh aspect, the present invention provides a polypeptide comprising an antibody heavy chain constant domain (CH domain) comprising an N-glycosylation site at asparagine N276, particularly generated due to the replacement of Y278 by S278 (Y278→S278), and/or an N-glycosylation site at asparagine N159, particularly generated due to the replacement of G161 by S161 (G161→S161) (all numbered according to the Kabat numbering system).

Preferably, the above mentioned polypeptide further comprises 1 or 2 of the following structures —NG-cF*
attached to the N-glycosylation sites asparagine N276 and/or asparagine N159 comprised in said antibody heavy chain constant domain (CH domain), wherein
NG is an N-linked glycomoiety of said antibody, and
cF* is a core fucose analogue.

The fucose analogue may be a fucose analogue as described with respect to the first aspect of the invention. It is particularly preferred that the fucose analogue is a per-acetylated fucose analogue, preferably a pyranosyl form of 1,2,3,4-tetraacetyl-azido-fucose, more preferably a pyranosyl form of 1,2,3,4-tetraacetyl-azido-6-fucose.

The antibody heavy chain constant domain comprised in said polypeptide may further comprise an (naturally) N-glycosylation site at asparagine N297. To this N-glycosylation site the above-mentioned structure —NG-cF* may further be attached.

Preferably, the above-described antibody heavy chain constant domain comprised in said polypeptide has an amino acid sequence according to SEQ ID NO: 8 or SEQ ID NO: 9, wherein the amino acids G161 (CH) and/or Y278 (CH) (numbered according to the Kabat numbering system) are substituted with serine. Also encompassed are variants, particularly functionally active variants, of said sequences (see first aspect of the invention).

The above-described polypeptide may further comprise one or more, e.g. 1, 2, 3, or 4, preferably 1 or 2, EGF-like repeats comprising a serine and/or threonine residue. Said EGF-like repeats may have an amino acid sequence according to SEQ ID NO: 10. Also encompassed are variants of SEQ ID NO: 10 (see first aspect of the invention). Said EGF-like repeat (e.g. SEQ ID NO: 10) may be comprised at the N-terminus and/or C-terminus of said polypeptide.

To said serine and/or threonine residue comprised in the one or more, e.g. 1, 2, 3, or 4, preferably 1 or 2, EGF-like repeats, the following structure: —F*
may further be added, wherein F* is a fucose analogue moiety directly linked to said serine and/or threonine residue comprised in said EGF-like repeat(s).

In a further aspect, the present invention provides an antibody comprising two of the polypeptides as defined in the eleventh aspect, preferably an antibody comprising two of the fucose analogue comprising polypeptides as defined in the eleventh aspect. Such an antibody (without EGF-like repeats) may enable, for example, the synthesis of defined (immuno)conjugates having 2 to 6 pharmaceutically active compounds covalently linked per antibody molecule (1 to 3 per CH domain comprised in each polypeptide), or such an antibody (with EGF-like repeats) may enable, for example, the synthesis of defined (immuno)conjugates having 3 to 10 pharmaceutically active compounds covalently linked per antibody molecule (1 to 3 per CH domain comprised in each polypeptide and 1 or 2 EGF-like repeats attached to the N-terminus and/or C-terminus of each polypeptide).

In a twelfth aspect, the present invention provides a polypeptide comprising one or more, e.g. 1, 2, 3, or 4, preferably 1 or 2, EGF-like repeats comprising a serine and/or threonine residue. Said EGF-like repeats may have an amino acid sequence according to SEQ ID NO: 10. Also encompassed are variants of SEQ ID NO: 10 (see first aspect of the invention). Said EGF-like repeat (e.g. SEQ ID NO: 10) may be comprised at the N-terminus and/or C-terminus of said polypeptide. As to the definition of the EGF-like repeats it is referred to the first aspect of the present invention. Said EGF-like repeats are preferably repeats which are naturally not comprised in said polypeptide, thus, artificial EGF-like repeats.

To said serine and/or threonine residue comprised in the one or more, e.g. 1, 2, 3, or 4, preferably 1 or 2, EGF-like repeats, the following structure: —F*
is preferably further added, wherein F* is a fucose analogue moiety directly linked to said serine and/or threonine residue comprised in said EGF-like repeat(s).

The fucose analogue may be a fucose analogue as described with respect to the first aspect of the invention. It is particularly preferred that the fucose analogue is a per-acetylated fucose analogue, preferably a pyranosyl form of 1,2,3,4-tetraacetyl-azido-fucose, more preferably a pyranosyl form of 1,2,3,4-tetraacetyl-azido-6-fucose.

In a further aspect, the present invention provides an antibody comprising two of the polypeptides as defined in the twelfth aspect, preferably an antibody comprising two of the fucose analogue comprising polypeptides as defined in the twelfth aspect.

In a thirteenth aspect, the present invention relates to a pharmaceutical composition comprising
(i) the polypeptide according to the eleventh aspect or a pharmaceutically acceptable salt thereof, or the polypeptide according to the twelfth aspect or a pharmaceutically acceptable salt thereof, or
(ii) the antibody comprising two polypeptides according to the eleventh aspect or a pharmaceutical acceptable salt thereof, or the antibody comprising two polypeptides according to the twelfth aspect or a pharmaceutically acceptable salt thereof.

Preferably, the pharmaceutical composition further comprises one or more pharmaceutically acceptable excipient(s) and/or carrier(s). As to the definition of the term "pharmaceutically acceptable salt", it is referred to the above. Preferred pharmaceutically acceptable excipient(s) and/or carrier(s) are also described above.

In another further aspect, the present invention relates to methods for diagnosing an autoimmune disease, an infectious disease or cancer in a patient by administering an effective amount of immunoconjugate that binds to an antigen associated with the autoimmune disease, and detecting the immunoconjugate in the patient. In yet another aspect, a virus or vaccine antigen, decorated with the fucose analogue by having said virus or vaccine antigen being produced by the engineered cell of the present invention, can be linked to a conjugate that serves as vaccine adjuvant (such as squalene or CpG DNA), or that helps to target the vaccine antigen to antigen-presenting cells (for example, by linkage to a ligand for toll-like receptors), or that interferes with infectivity to support attenuation (weakening) of the thus treated virus (for example by inducing crosslinkage with doubly functionalized conjugates), or that labels the virus with a dye such as ALEXA or FITC to allow visualization of the infection in tissue culture or living organism.

In a further aspect, the present invention relates to a kit of parts comprising a eukaryotic cell for producing a molecule comprising a fucose analogue, wherein in said cell the GDP-L-fucose synthesis pathway originating from GDP-D mannose is blocked and a GDP-fucose analogue. In another further aspect, the present invention relates to a cell culture system comprising a eukaryotic cell for producing a molecule comprising a fucose analogue, wherein in said cell the GDP-L-fucose synthesis pathway originating from GDP-D mannose is blocked and comprising a fucose analogue in the cell culture medium. All terms used in the description of these aspects have meaning as described above.

Various modifications and variations of the invention will be apparent to those skilled in the art without departing from the scope of invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art in the relevant fields are intended to be covered by the present invention.

Some of the amino acid sequences described herein are summarized as follows:

```
                                              SEQ ID NO: 8
(IgG1 CH Allele 01, human)
ASTKGPSVFP LAPSSKSTSG GTAALGCLVK

DYFPEPVTVS WNSGALTSGV HTFPAVLQSS GLYSLSSVVT

VPSSSLGTQT YICNVNHKPS NTKVDKKVEP KSCDKTHTCP

PCPAPELLGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSRDE LTKNQVSLTC LVKGFYPSDI AVEWESNGQP

ENNYKTTPPV LDSDGSFFLY SKLTVDKSRW QQGNVFSCSV

MHEALHNHYT QKSLSLSPGK

SEQ ID NO: 9
(IgG1 CH Allele 02, human)
ASTKGPSVFP LAPSSKSTSG GTAALGCLVK

DYFPEPVTVS WNSGALTSGV HTFPAVLQSS GLYSLSSVVT

VPSSSLGTQT YICNVNHKPS NTKVDKKVEP KSCDKTHTCP

PCPAPELLGG PSVFLFPPKP KDTLMISRTP EVTCVVVDVS

HEDPEVKFNW YVDGVEVHNA KTKPREEQYN STYRVVSVLT

VLHQDWLNGK EYKCKVSNKA LPAPIEKTIS KAKGQPREPQ

VYTLPPSREE MTKNQVSLTC LVKGFYPSDI AVEWESNGQP

ENNYKTTPPV LDSDGSFFLY SKLTVDKSRW QQGNVFSCSV

MHEALHNHYT QKSLSLSPGK

SEQ ID NO: 10
(EGF-like repeat)
DGDGCASSPCQNGGSCKDQLQSYIC
```

The following figures and examples are merely illustrative of the present invention and should not be construed to limit the scope of invention as indicated by the appended claims in any way.

REFERENCES

Campbell, C. and Stanley, P. (1983) Regulatory mutations in CHO cells induce expression of the mouse embryonic antigen SSEA-1. Cell, 35, 303-309.

Chen, W., Tang, J., Stanley, P. Suppressors of α(1,3)fucosylation identified by expression cloning in the LEC11B gain-of-function CHO mutant Glycobiology (2005) 15(3): 259-269

Howard, D. R., Fukuda, M., Fukuda, M. N., and Stanley, P. (1987) The GDP-fucose:N-acetylglucosaminide 3-alpha-L-fucosyltransferases of LEC11 and LEC12 Chinese hamster ovary mutants exhibit novel specificities for glycolipid substrates. J. Biol. Chem., 262, 16830-16837.

Zhang, A., Potvin, B., Zaiman, A., Chen, W., Kumar, R., Phillips, L., and Stanley, P. (1999) The gain-of-function Chinese hamster ovary mutant LEC11B expresses one of two Chinese hamster FUT6 genes due to the loss of a negative regulatory factor. J. Biol. Chem., 274, 10439-10450.

EXAMPLES

Cell Lines

The recombinant CHO/DG44 cell line CHO-IgG was established earlier in our laboratory by stable transfection of the dihydrofolate reductase-deficient CHO cell line, CHO/DG44 (Urlaub et al., 1986, Proc Natl Acad Sci USA. 83 (2): 337-341) with an expression vector containing an antibody expression cassette comprising nucleotide sequences encoding light and heavy chain of a therapeutic monoclonal antibody (Trastuzumab (Herceptin®)). Generation of the cell line RMD-CHO-IgG started from the existing CHO-IgG cell line. Both cell lines were maintained in serum-free medium.

Gene Optimization and Synthesis

The amino acid sequence for the oxidoreductase Rmd (*Pseudomonas aeruginosa* PAO1; 304 amino acids) (GenBank Accession No. GenBank: AAG08839.1) was reverse translated and the resulting nucleotide sequence optimized by knockout of cryptic splice sites and RNA destabilizing sequence elements, optimisation for increased RNA stability and adaptation of codon usage to match the requirements of CHO cells (*Cricetulus griseus*).

Construction of the RMD Expression Plasmid

The synthesized RMD-construct was cut with EcoRI and Bgl II and dephoshorylated with calf intestinal phosphatase. The digested and dephosphorylated insert was ligated into a pre-digested bicistronic expression vector which allows coordinated co-expression of RMD and green fluorescent protein from a bicistronic message (gfp). The expression plasmid is equipped with a Neomycin resistance gene allowing for direct selection of cells that have stably integrated the bicistronic expression cassette. General procedures for constructing expression plasmids are described in Sambrook, J., E. F. Fritsch and T. Maniatis: Cloning I/II/III, A Laboratory Manual New York/Cold Spring Harbor Laboratory Press, 1989, Second Edition.

Figure 1:
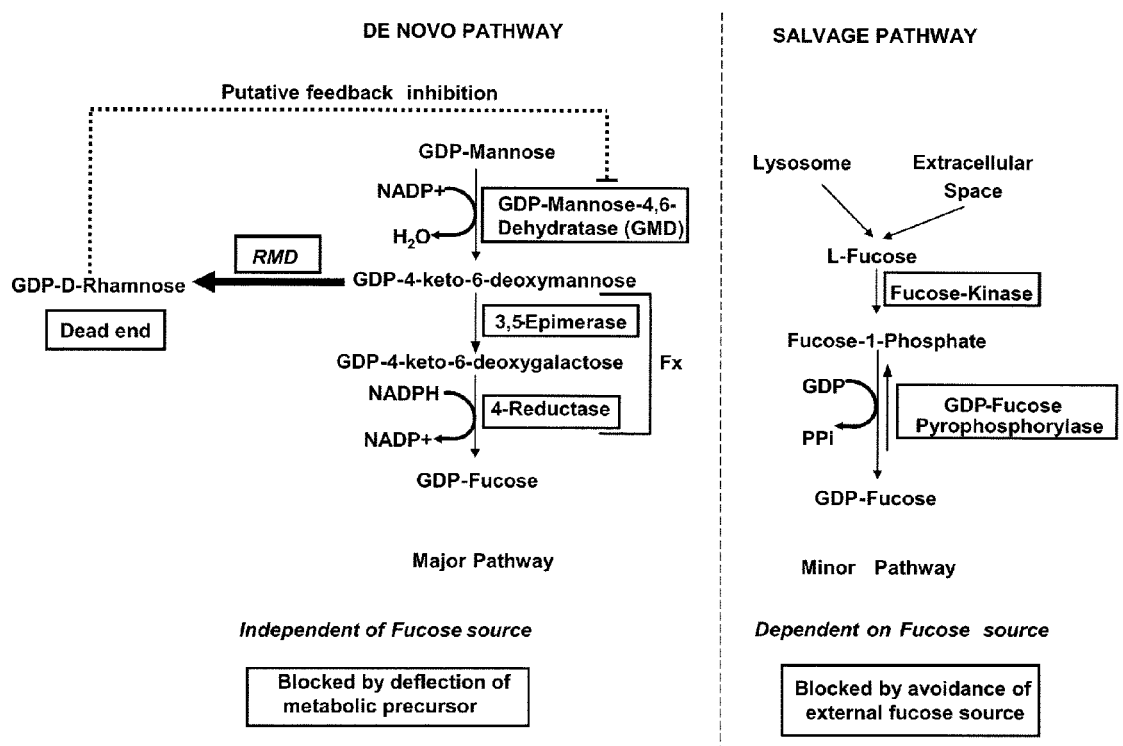
FIG. 1 shows an overview of the fucose salvage and de novo pathways in eukaryotic cells (e.g. vertrebrate cells). In the absence of fucose, cells are unable to synthesize GDP-fucose via the salvage pathway (see right hand panel). The de novo pathway can be blocked by enzymatic conversion of the intermediate GDP-4-keto-6-deoxymannose into a dead end product that typically does not occur in vertebrate cells (left hand panel). If the deflecting enzyme is RMD, for example, then the dead end product is GDP-D-rhamnose. GDP-deoxyhexoses such as GDP-D-rhamnose may exert a feedback inhibition on the GMD-enzyme thereby further blocking the fucose de novo pathway as well as the alternate GDP-rhamnose synthesis.
Figure 2:
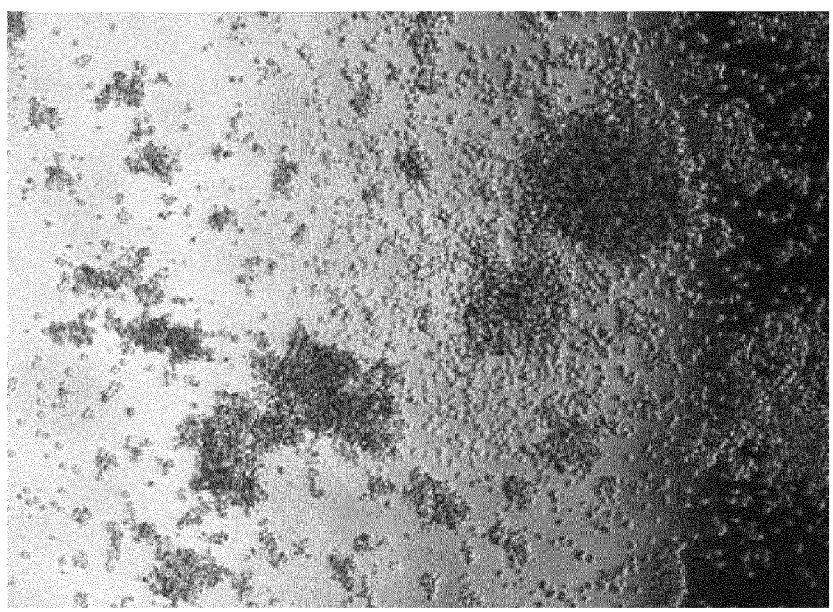
FIG. 2 shows GFP-fluorescence of RMD-CHO-IgG cells that stably overexpress the RMD transgene.
Figure 2:
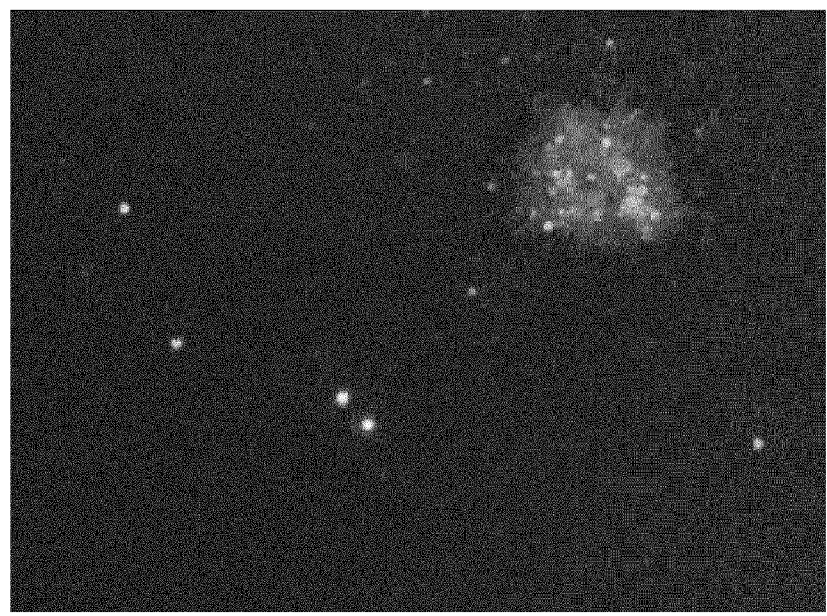

Conversion of Antibody-Producing CHO-IgG Cells into Cells Having a Blocked De Novo Pathway CHO-IgG cells stably expressing the IgG1-type therapeutic antibody Trastuzumab were stably transfected with the RMD-gfp transgene by electroporation according to the manufacturer's instructions (MicroPorator, PEQLAB Biotech, Germany). 24 h after electroporation transfectants were selected in alpha-MEM containing the antibiotic G418. The G418-resistant clones were then isolated by limiting dilution cloning, i.e. they were resuspended in this selective medium and seeded into 96 well plates at dilutions where the likelihood of obtaining a colony from a single cell is greater 95% based on poisson statistics. To assure monoclonality, cells grown within the 96 wells were isolated and again seeded into 96 well plates at limiting dilution. After these two rounds of single cell cloning, a couple of the isolated single cell clones were expanded into larger volumes. Afterwards, they were adapted to growth in suspension. Using the described electroporation protocol a transformation efficiency of approximately 2000 per $2\times10^6$ electroporated cells was achieved as assessed from gfp-fluorescence distribution in the culture dishes (FIG. 2).

Clone Screening by Fluorescence Microscopy

Figure 3:
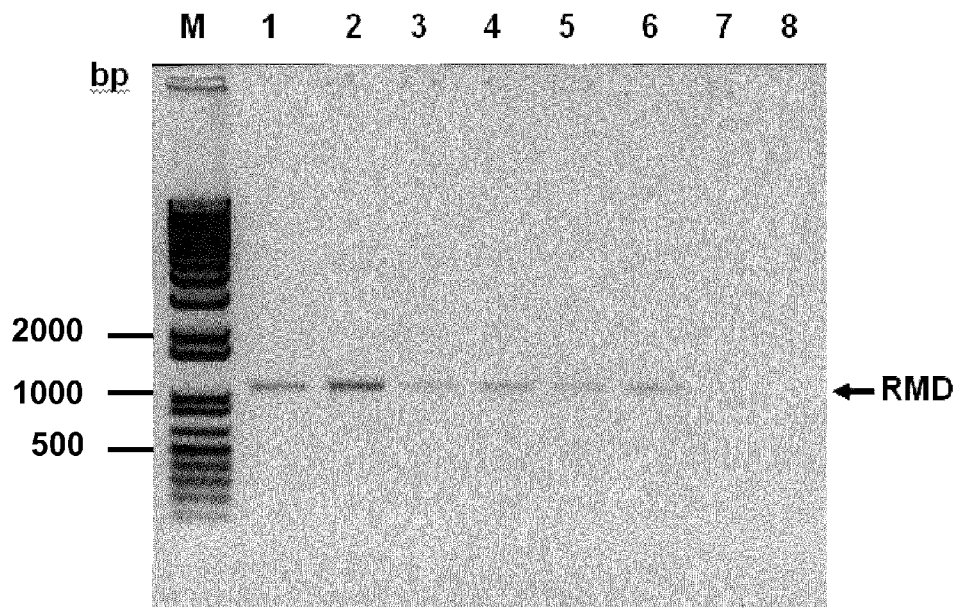
FIG. 3 shows a RT-PCR analysis of clones expressing the RMD-Transgene. Lane M=bp-DNA-Marker, Lane 1: RMD-CHO-IgG clone 1; Lane 2: RMD-CHO-IgG clone 2; Lane 3: RMD-CHO-IgG clone 3; Lane 4: RMD-CHO-IgG clone 4; Lane 5: RMD-CHO-IgG clone 5; Lane 6: RMD-CHO-IgG clone 6; Lane 7: CHO-IgG parental clone; Lane 8: negative PCR control. The RMD band is visible in all RMD-transfected clones.

Single cell clones were seeded into 96 well plates and screened for successful RMD-integration by monitoring of GFP-fluorescence with an Olympus IX-50 (Olympus Optical Co., Europe) fitted with a cmount adapter. For GFP-scan a fluorescence-filter at 200-fold extension was used versus phase contrast. Images were edited by Viewfinder lite application. Additionally, mRNA expression of the RMD transgene was confirmed by RT-PCR analysis. Successful expression of the RMD transgene was confirmed by RT-PCR using an RMD-specific set of primers (FIG. 3).

Figure 4:
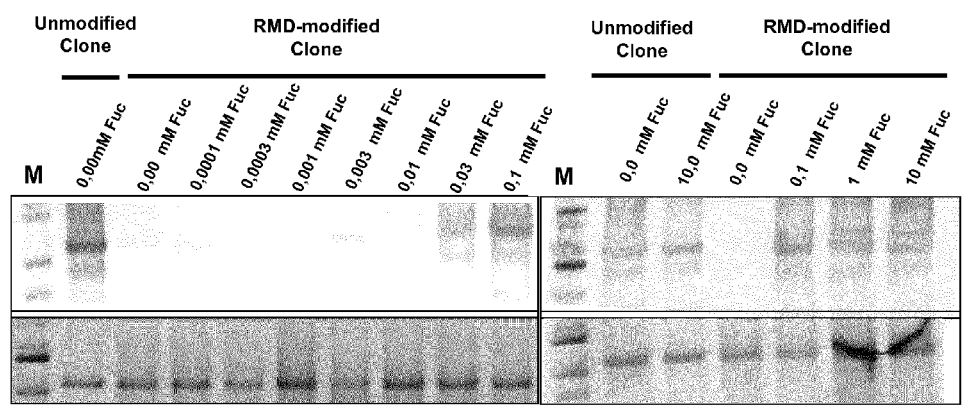
FIG. 4 shows the determination of the minimum required fucose analogue concentration to achieve restoration of the core-fucosylation status of antibodies secreted from an RMD-modified cell line.

Fucose Feeding Experiment:

Determination of the Minimum Required Amount of Fucose Analogue in Culture Medium:

Currently, Fucose analogs are not routinely used in cell culture and are thus still expensive. In order to identify the most cost efficient fucose analogue concentration, we needed to determine the minimum required amount of fucose analogue that was sufficient to completely rescue the fucosylation status of heterologously expressed antibodies secreted from RMD-co-expressing cells. Antibody expressing CHO cells carrying the RMD transgene were cultured in medium containing varying concentrations of fucose and fed with a feed mix supplemented with that same amount of fucose. Cells were grown for 12 days before harvesting the cell culture supernatant. The supernatants were analysed by lectin blotting using biotinylated PSA lectin (*pisum sativum*) that specifically recognizes the alpha-1,6-linked core-fucose. Lectin blotting was conducted using the Vecstatin Elite ABC Kit (Vector Labs, USA) according to the manufacturers instructions. FIG. 4 demonstrates that an almost complete rescue of core-fucosylation was achieved when media and feeds were supplemented with 0.03 mM Fucose.

Production of Monoclonal Antibodies Comprising a Fucose Analogue on their N-Linked Glycomoieties Antibody expressing CHO cells carrying the RMD transgene are cultured in medium containing 0.03 mM 1,2,3,4-tetraacetyl-6-azido-fucose (custom synthesized by Glykoteam GmbH Hamburg) and fed with a feed mix supplemented with 0.03 mM 1,2,3,4-tetraacetyl-6-azido-fucose. Cells are inoculated at $2\times105$ cells/ml in said growth medium. The shaker tubes are incubated at 180 rpm, 37° C., 7.5% pCO2. The culture is stopped after 7 days when the cells still showed a vitality>80% and cell culture supernatants are harvested. Viable cell density is measured with an automatic cell counter, Vi-CELL™ XR (Beckman Coulter, Fullerton, Calif.), using trypan blue exclusion.

Purification of Fucose Analogue Containing Monoclonal Antibodies by Protein A Affinity Chromatography Fucose analogue containing antibodies secreted from these cells are purified by protein A affinity chromatography. Following sterile filtration by 0.2 µm filter, the supernatant is loaded onto a Protein-A-Sepharose mini column. 0.5 ml column support material with a total capacity of 10 mg are used. The column is equilibrated with 5 column volumes of 20 mM sodium phosphate, pH 7.0 at gravity flow. After protein binding at a slow flow rate, the column was washed twice with the equilibration buffer. Then the antibody is eluted with 4 column volumes 0.1 M glycine buffer, pH 3.0 at gravity flow. Fractions of 1 ml are collected and immediately neutralized with 1 M Tris-HCl, pH 9.

Labelling Azido-Fucose Containing Antibodies with Alkynyl-Biotin

The purified antibody containing 6-azido-fucose linked to its N-glycan core-position is subjected to a copper-mediated click chemistry coupling reaction with Biotin alkyne (Cat. No. B10185, Invitrogen). The click reaction is performed as described in the Click-iT® Protein Reaction Buffer Kit (Catalog no. C10276 (Invitrogen, Life Technologies Inc.) according to the manufacturers instructions. Briefly, the following components are added to a 1.5 mL microcentrifuge tube:

200 µg in a maximum volume of 50 µL of azido-fucose-labeled antibody in 50 mM Tris-HCl, pH 8.0
  100 µL of the Click-iT® reaction buffer from the kit containing a final concentration of 40 µM alkynyl-Biotin.
  Sufficient volume of 18 megaOhm water for a final volume of 160 µL The tube is then capped and vortexed for 5 seconds. 10 µL of CuSO4 (Component B) are added and the tube is again vortexed for 5 seconds. Then, 10 µL of Click-iT® reaction buffer additive 1 solution from the kit are added and the tube is again vortexed for 5 seconds. After 2-3 minutes, but not longer than 5 minutes, 20 µL of Click-iT® reaction buffer additive 2 solution are added and the tube is again vortexed for 5 seconds. The tube is then rotated end-over-end for 20 minutes using a rotator.

Analysis of Biotin-Labelled Antibodies
Part I Determination of Labelling Specificity:

600 μL of methanol are added to the reaction mixture and the mixture is briefly vortexed. 150 μL of chloroform are added and the mixture is vorteced briefly. 400 μL of 18 megaOhm water are then added and the mixture is vortexed briefly. The tube is then centrifuged for 5 minutes at 13,000× g, then carefully removed and as much of the upper aqueous phase as possible is discarded while leaving the interface layer containing the protein precipitate intact. Note: The upper phase is bright orange. The lower phase is colorless if biotin is used. 450 μL of methanol are then added to the tube and the tube is again vortexed briefly. The tube is then centrifuged for 5 minutes at 13,000×g to pellet the protein. The supernatant is discarded. Again 450 μL of methanol are added to the tube and the tube is vortexed briefly. The tube is again centrifuged and the supernatant is discarded. The pellet is allowed to air-dry for 15 minutes at ambient temperature and then resolubilized in non-reducing 1D gel electrophoresis sample loading buffer.

Samples are separated on 1D SDS-PAGE gels with and without reducing agent TCEP (Invitrogen) and blotted to a PVDF membrane (Immobilon-P (PVDF-Membrane 0.2 μm) [Millipore, Cat. IPVH00010]). The blotted PVDF membrane is blocked 30 min. at RT with 1× Carbo-Free Blocking solution ([VectorLabs Cat. No. SP5040], Vector Labs, USA) and then incubated with Streptavidin-HRP-conjugate (VECTASTATIN Elite ABC Kit; VectorLabs Cat. No. PK6100, Vector Labs, USA). The blotmembrane is then washed 3×5 min in PBS-T (1×PBS [pH 7.4]+0.05% Tween 20). TMB-substrate [Seramun, Cat. S-002-2-TMB prec] is dispersed across the blot membrane and the membrane is incubated for 0.5-5 min at ambient temperature. The reaction is stopped by washing with MilliQ $H_2O$. The developed membrane is then air-dried and scanned. In the non-reduced sample lane a band at approximately 150 KDa apparent molecular mass is detected, representing the full length antibody. In the reducing sample lane, only the band migrating at an apparent molecular weight of 50 KDa, representing the heavy chain is detected as a biotinylated band whereas the light chain band migrating at ~25 KDa apparent molecular mass is only detected after secondary Coomassie staining. This result demonstates that the label has specifically attached to the heavy chain which is in line with the expectation that labelled fucose residues are exclusively found on the glycomoiety linked to ASN 297 (Kabat) of the heavy chain.

Part II: Assessment of Labelling Efficiency

In order to determine the efficiency of the Fucose-mediated labelling, we needed to determine the remaining amount of unlabelled N-glycans per antibody. The avidin-biotin complex is the strongest known noncovalent interaction (Ka=1015 M−1) between a protein and ligand. The bond formation between biotin and avidin is rapid and, once formed, is unaffected by extremes of pH, temperature, organic solvents and most denaturing agents. Monovalent streptavidin is an engineered recombinant form of streptavidin which is a tetramer but only one of the four binding sites is functional. [Horvath et al. 2006] This single binding site has 10-14 mol/L affinity and cannot cause cross-linking Bound monovalent streptavidin causes a biotinylated antibody to shift its apparent molecular mass in nondenaturing SDS-PAGE (Humbert et al. 2005) by 60 KDa per presented biotin, if monovalent steptavidin is available in excess during complex formation. 10 μg of click-reacted, biotinylated antibody sample is incubated with 10 μg (an excess amount) of monovalent Streptavidin (60 KDa) (xxx) and then analyzed on a NuPAGE 4-12% gel using the buffers of Kasarda et al. (2010). Bands representing molecular masses of 60, 150, 210 and 270 KDa indicate free streptavidin (60 KDa), completely unconjugated antibody (150 KDa), antibody with one biotinylated fucose residue (210 KDa), antibody with fully biotinylated fucose residue (270 KDa). Labelling efficiency is calculated from the ratio of fully biotinylated antibody and unbound or singly biotinylated antibody molecules.

The invention claimed is:

1. A eukaryotic cell for producing a molecule comprising a fucose analogue, wherein
   (i) in said cell the GDP-L-fucose synthesis pathway originating from GDP-D-mannose is blocked due to the presence of at least one enzyme which uses GDP-6-deoxy-D-lyxo-4-hexulose as a substrate, wherein the enzyme does not catalyze the reaction which converts GDP-6-deoxy-D-lyxo-4-hexulose into GDP-L-fucose, and
   (ii) said cell comprises a GDP-L-fucose analogue, wherein the GDP-L-fucose analogue is a substrate for a fucosyltransferase and enters the cell from extracellular medium.

2. The cell of claim 1, wherein the enzyme which uses GDP-6-deoxy-D-lyxo-4-hexulose as a substrate is selected from the group consisting of GDP-6-deoxy-D-lyxo-4-hexulose reductase (RMD), GDP-perosamine synthetase (Per), GDP-6-deoxy-D-talose synthetase (GTS), GDP-fucose synthetase Cys109Ser-(GFS-Cys109Ser) mutant, GDP-4-keto-6-deoxymannose-3-dehydratase (ColD), preferably GDP-4-keto-6-deoxymannose-3-dehydratase (ColD) in combination with GDP-L-colitose synthase (ColC), and variants thereof.

3. The cell of claim 1, wherein said cell
   (i) does not comprise an enzymatically active GDP-mannose dehydratase (GMD) or comprises a GDP-mannose dehydratase (GMD) having a reduced enzymatic activity,
   (ii) does not comprise an enzymatically active GDP-Fucose synthetase (GFS) or comprises a GDP-Fucose synthetase (GFS) having a reduced enzymatic activity, and/or
   (iii) does not comprise an enzymatically active alpha-1,3-fucosyltransferase.

4. The cell of claim 1, wherein the cell is a vertebrate cell.

5. The cell of claim 4, wherein the vertebrate cell is a mammalian, a fish, an amphibian, a reptilian cell or an avian cell.

6. The cell of claim 5, wherein
   (i) the mammalian cell is a human, hamster, canine or monkey cell,
   (ii) the fish cell is a *Ictalurus punctatus* (channel catfish) cell,
   (iii) the amphibian cell is a *Xenopus laevis* cell,
   (iv) the reptilian cell is an *Iguana iguana* cell, or
   (v) the avian cell is an avian retina cell, or an avian somite cell.

7. A method for producing a molecule which comprises a fucose analogue comprising the steps of:
   (i) providing a eukaryotic cell according to claim 1, and
   (ii) isolating the molecule comprising a fucose analogue from the cell in i).

8. The method of claim 7, further comprising the steps of:
   (iii) covalently coupling a pharmaceutically active compound via the fucose analogue to the molecule comprising said fucose analogue, thereby obtaining a conjugate comprising a molecule which comprises a fucose analogue and a pharmaceutically active compound.

9. A conjugate comprising a molecule which comprises a fucose analogue and a pharmaceutically active compound obtainable by the method of claim 8, wherein the pharmaceutically active compound is a cytotoxic drug or a pharmacokinetic half-life extender.

10. A conjugate which comprises a protein or polypeptide comprising one or more of the following structures: —NG-cF*—Yo-C,
    wherein each is attached to an N-glycosylation site comprised in said protein or polypeptide,
    NG is an N-linked glycomoiety of said protein or polypeptide,
    cF* is a core fucose analogue,
    Y is a spacer unit, wherein o is an integer of 0 or 1, and
    C is a pharmaceutically active compound,
    wherein the pharmaceutically active compound is a cytotoxic drug or a pharmacokinetic half-life extender.

11. The conjugate of claim 10, wherein the glycomoiety is an N-linked glycomoiety of the complex type.

12. The conjugate of claim 10, wherein the polypeptide is an antibody heavy chain (H).

13. A conjugate which comprises a protein or polypeptide comprising one or more EGF-like repeats comprising a serine and/or threonine residue to which the following structure: —F*-Yp-C
    is attached, wherein
    F* is a fucose analogue moiety directly linked to said serine and/or threonine residue,
    Y is a spacer unit, wherein p is an integer of 0 or 1, and
    C is a pharmaceutically active compound,
    wherein the EGF-like repeats have independently from each other an amino acid sequence according to SEQ ID NO: 10 or are a variant thereof which is at least 90% identical to the amino acid sequence according to SEQ ID NO: 10.

14. The conjugate of claim 13, wherein the polypeptide is an antibody heavy chain (H).

15. A conjugate which comprises a polypeptide comprising one or more of the following structures: —NG-cF*—$Y_o$—C,
- wherein each is attached to an N-glycosylation site comprised in said polypeptide,
- NG is an N-linked glycomoiety of said polypeptide,
- cF* is a core fucose analogue,
- Y is a spacer unit, wherein o is an integer of 0 or 1, and
- C is a pharmaceutically active compound,
- wherein the polypeptide is an antibody heavy chain (H).

16. An antibody comprising two conjugates as defined in claim 15.

17. The method of claim 1, wherein the GDP-L-fucose analogue comprises one or more reactive or activated substitutions selected from chemical groups listed in functional group A or functional group B of Table 2.

18. The method of claim 1, wherein the GDP-L-fucose analogue is a peracetylated fucose analogue.

* * * * *